(12) United States Patent
Iqbal et al.

(10) Patent No.: US 9,249,203 B2
(45) Date of Patent: *Feb. 2, 2016

(54) TREATMENT OF BRAIN INJURY WITH A NEUROTROPHIC PEPTIDE

(71) Applicant: The Research Foundation for Mental Hygiene, Inc., Menands, NY (US)

(72) Inventors: Khalid Iqbal, Staten Island, NY (US); Inge Grundke-Iqbal, Staten Island, NY (US)

(73) Assignee: The Research Foundation For Mental Hygiene, Inc., Menands, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/325,880

(22) Filed: Jul. 8, 2014

(65) Prior Publication Data

US 2015/0252087 A1    Sep. 10, 2015

Related U.S. Application Data

(63) Continuation-in-part of application No. 13/676,649, filed on Nov. 14, 2012, now Pat. No. 8,796,215, which is a continuation-in-part of application No. 13/044,323, filed on Mar. 9, 2011, now Pat. No. 8,592,374, which is a continuation-in-part of application No. 12/531,616, filed as application No. PCT/EP2008/002106 on Mar. 17, 2008, now Pat. No. 8,338,378.

(30) Foreign Application Priority Data

Mar. 16, 2007   (EP) ..................................... 07450050

(51) Int. Cl.
| | |
|---|---|
| *A01N 37/18* | (2006.01) |
| *A61K 38/16* | (2006.01) |
| *C07K 14/475* | (2006.01) |
| *A61K 38/08* | (2006.01) |
| *A61K 38/18* | (2006.01) |
| *C07K 5/103* | (2006.01) |
| *C07K 5/113* | (2006.01) |
| *C07K 7/06* | (2006.01) |

(52) U.S. Cl.
CPC ............... *C07K 14/475* (2013.01); *A61K 38/08* (2013.01); *A61K 38/185* (2013.01); *C07K 5/101* (2013.01); *C07K 5/1008* (2013.01); *C07K 5/1021* (2013.01); *C07K 7/06* (2013.01)

(58) Field of Classification Search
None
See application file for complete search history.

(56) References Cited

U.S. PATENT DOCUMENTS 8,338,378 B2 * 12/2012 Mossler et al. .............. 514/17.7

* cited by examiner

*Primary Examiner* — Olga N Chernyshev
(74) *Attorney, Agent, or Firm* — David L. Nocilly; Bond Schoeneck & King, PLLC

(57) ABSTRACT

A neurotrophic peptide having the sequence VGDG-GLFEKKL (SEQ ID NO: 1) may be used to help sustain local microenvironment after mild-to-moderate brain injury. Treatment with the peptide was shown to enhance differentiation of newly born progenitors in the dentate gyrus 30 days after injury and to promote neuronal maturation and survival that is not seen naturally after traumatic brain injuries.

7 Claims, 29 Drawing Sheets

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: neurotrophic and/or neurogenic peptide

<400> SEQUENCE: 1

Val Gly Asp Gly Gly Leu Phe Glu Lys Lys Leu
1               5                   10
```

TREATMENT OF BRAIN INJURY WITH A NEUROTROPHIC PEPTIDE

CROSS-REFERENCE TO RELATED APPLICATIONS

The present application is a continuation-in-part of U.S. patent application Ser. No. 13/676,649, filed on Nov. 11, 2012, which is a continuation-in-part of Ser. No. 13/044,323, filed on Mar. 9, 2011, which is a continuation-in-part of U.S. patent application Ser. No. 12/531,616 filed Sep. 16, 2009, which is a national stage application of PCT/EP2008/002106, filed on Mar. 17, 2008, which claims priority to European Application No. 07450050.5 filed Mar. 16, 2007, all of which are hereby incorporated by reference in their entireties.

BACKGROUND OF THE INVENTION

1. Field of the Invention

The present invention relates to neurotrophic and/or neurogenic peptides and their use for treating traumatic brain injuries.

2. Description of the Related Art

Traumatic Brain Injury (TBI) is the leading cause of death and disability in children and adults from ages 1 to 44 with an annual incidence of 1.7 million in the US, causing enormous economic burden and no proven therapy to improve long-term outcomes. Owing to the inherent vulnerability of hippocampus to trauma, cognitive impairment is widely accepted as the most devastating deficit in long-term survivors of TBI. In fact, hippocampal neuronal loss accompanies >80% of fatal TBI and apoptotic events in the hippocampus can be observed up to 12 months following TBI.

Observations from experimental models of TBI indicate enhanced stem cell proliferation in the hippocampal dentate gyrus (DG) following TBI and is widely considered an endogenous repair mechanism to counter cognitive decline after brain trauma. The biological drive behind increased stem cell proliferation in the hippocampus is based, in part, on neurotrophic factor dynamics within the local microenvironment. Consequently, increasing adult hippocampal neurogenesis and stimulating neuronal plasticity pharmacologically is considered a very useful strategy towards inhibiting cognitive decline following TBI.

Supplementing the hippocampus with neurotrophic factors that drive stem cells towards differentiation and sustain local microenvironment is a powerful concept in neuropharma. Several studies have reported enhancement of neurogenesis in TBI models through neurotrophic factor supplementation such as S100B, erthyropoietin, EGF and FGF and superior performance in memory tasks. While the administration of neurotrophic factors has generated much excitement in the literature, invasive mode of delivery, adverse side effects and difficult pharmacokinetics have very much limited the clinical usefulness of this approach

BRIEF SUMMARY OF THE INVENTION

The present invention comprises the use of an 11-mer peptide based on a biologically active region of human Ciliary Neurotrophic Factor (CNTF). This peptide, referred to as Peptide 6 and having the sequence VGDGGLFEKKL (SEQ ID NO: 1) has been shown to have significant neurogenic and neurotrophic effects in the DG of normal adult C57BL6 mice, as well as transgenic mouse models of Down syndrome and Alzheimer disease (AD), disorders with documented abnormal hippocampal neurogenesis and cognitive impairment. Chronic administration of Peptide 6 to a controlled cortical impact (CCI)-mouse model of mild-to-moderate TBI resulted in increased neuronal differentiation of progenitors in the DG. Furthermore, 30-day administration of Peptide 6 ameliorated TBI-induced decrease in dendritic and synaptic density in DG and CA1 regions of the hippocampus. There was also significant increase in the immunoreactivity of immediate-early gene zif268 in the CA1 region, indicating increased neuronal activity and activation of the traditional excitatory tri-synaptic pathway in the hippocampus.

The inorganic cation at the C-terminal end of the peptide according to the present invention may be an alkali metal or alkali earth metal cation, preferably a lithium, sodium, potassium, magnesium or calcium cation. These inorganic cations are regularly used to prepare salts of pharmaceutically active substances. The organic cation may be a quaternary ammonium ion.

If the N-terminal end of the peptide according to the present invention comprises a positive charge, said charge may be preferably compensated by an equivalent of an inorganic or organic anion. The organic anion can be, for instance, acetate anion.

The peptides according to the present invention may be formulated in a pharmaceutical preparation, which can be administered to a patient for treating tramautic brain injuries. The pharmaceutical preparation may further comprise pharmaceutically acceptable excipients and/or carriers.

The pharmaceutical preparation according to the present invention may comprise, in addition to the peptide according to the present invention, further active components, which may exhibit similar properties when administered to an individual or which may cause other reactions in the treated patient. Antioxidants like vitamins may be considered as further active components because antioxidants inhibit oxidation or suppress reactions promoted by oxygen, oxygen free radicals, oxygen reactive species including peroxides. Antioxidants, especially lipid-soluble antioxidants, can be absorbed into the cell membrane to neutralize oxygen radicals and thereby protect the membrane. The antioxidants useful in the present invention are preferably vitamin antioxidants that may be selected from the group consisting of all forms of Vitamin A including retinal and 3, 4-didehydroretinal, all forms of carotene such as alpha-carotene, beta-carotene, gamma carotene, delta-carotene, all forms of Vitamin C (D-ascorbic acid, L-ascorbic acid), all forms of tocopherol such as Vitamin E (Alpha-tocopherol, 3,4-dihydro-2,5,7,8-tetramethyl-2-(4,8,12-trimethyltri-decyl)-2H-1-benzopyran-6-ol), beta-tocopherol, gamma-tocopherol, delta-tocopherol, tocoquinone, tocotrienol and Vitamin E esters which readily undergo hydrolysis to Vitamin E such as Vitamin E acetate and Vitamin E succinate, and pharmaceutically acceptable Vitamin E salts such as Vitamin E phosphate, prodrugs of Vitamin A, carotene, Vitamin C, and Vitamin E, pharmaceutically acceptable salts of Vitamin A, carotene, Vitamin C, and Vitamin E, and the like, and mixtures thereof.

The present invention may be provided for intravenous, intramuscular, spinal, epidural, transdermal, intranasal, mucosal, parenteral, oral, enteral or rectal administration. Depending on the route of administration the pharmaceutical composition according to the present invention may be formulated, for instance, as tablets, capsules, liquids, infusion and suppositories. The peptides are preferably comprised in the composition in an amount between 0.1 µg/g to 100 mg/g, preferably 1 µg/g to 80 mg/g. In any way, the effective dosages for prevention or treatment of human patients can be optimised for given patients or patient collectives according to the routine methods available for the present field.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1A is the experimental paradigm where C57BL6 female mice were subjected to controlled cortical impact (CCI) of 1.5 mm deformation and received twice daily injections of BrdU (75 mg/kg) for two days and either saline or Peptide 6 (50 nmol/animal/day), one day after injury for 30 days. Mice were sacrificed on day 30;

FIG. 1B is a schematic of CNTF showing an a-helical molecule with secondary structure consisting of four antiparallel α-helices. Five regions (represented in different colors) correspond to the epitopes of neutralizing anti-human CNTF antibodies (adapted with permission from Chohan et al. 201119). Peptide 6 corresponds to VGDGGLFEKKL (SEQ. ID. NO: 1) epitope and contains the critical D1 cap region-binding site of CNTF receptor complex;

FIG. 1C is a schematic representation of mouse brain, coronal section, with side of injury (arrows, left) and colored areas depicting functional regions (right); where rSpA: retrosplenial area; pMA: primary motor area; sMA: secondary motor area; pSA: primary sensory area; pAuA: primary auditory area; TAsA: temporal association area; EntA: entorhinal area; Peri: perirhinal area; EntAl: lateral entorhinal area; PyrA: pryiform area; DG: dentate gyrus FIG. 1D is a representative T2W MRI sequence of a TBI mouse 30 days after CCI injury. Note that although brain deformation was kept at 1.5 mm, T2 signal change was seen beyond the contusion and into the hippocampal area;

Figure 2A:
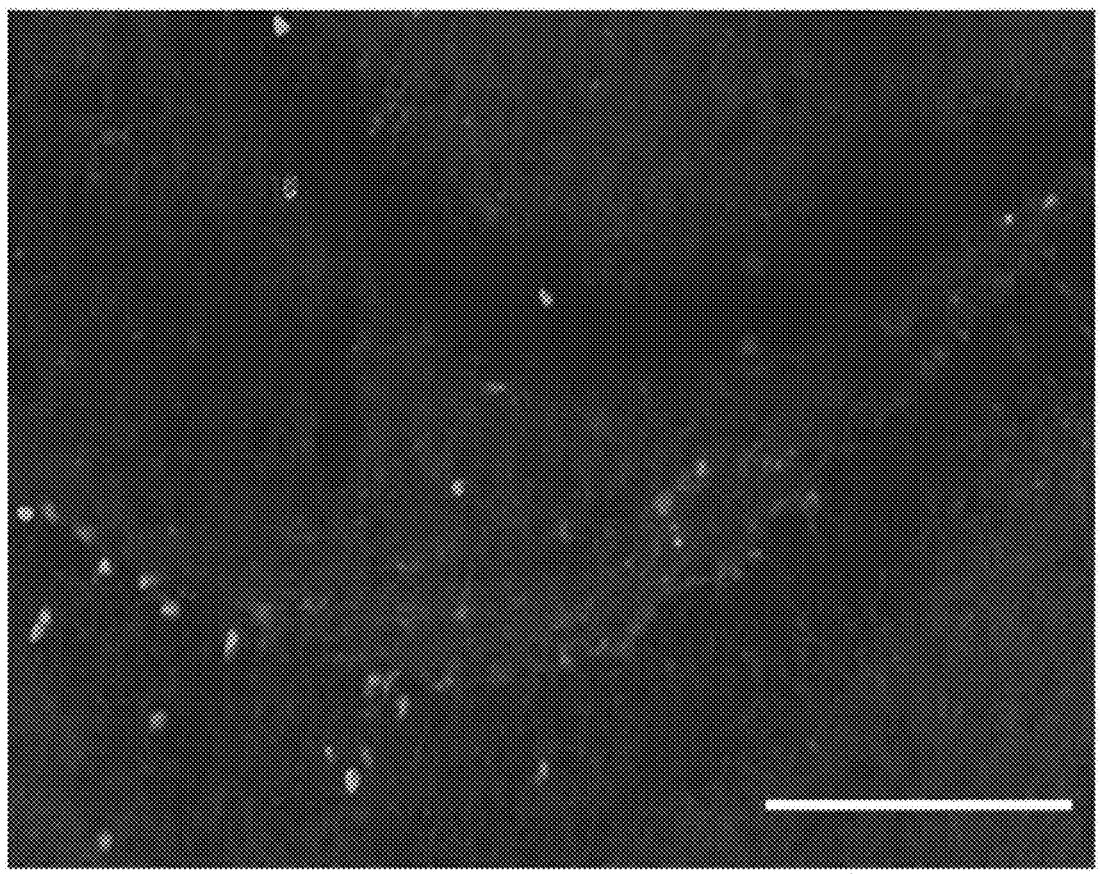
FIG. 2A is an image showing stem cell proliferation in a TBI mouse 30 days after injury.
Figure 2B:
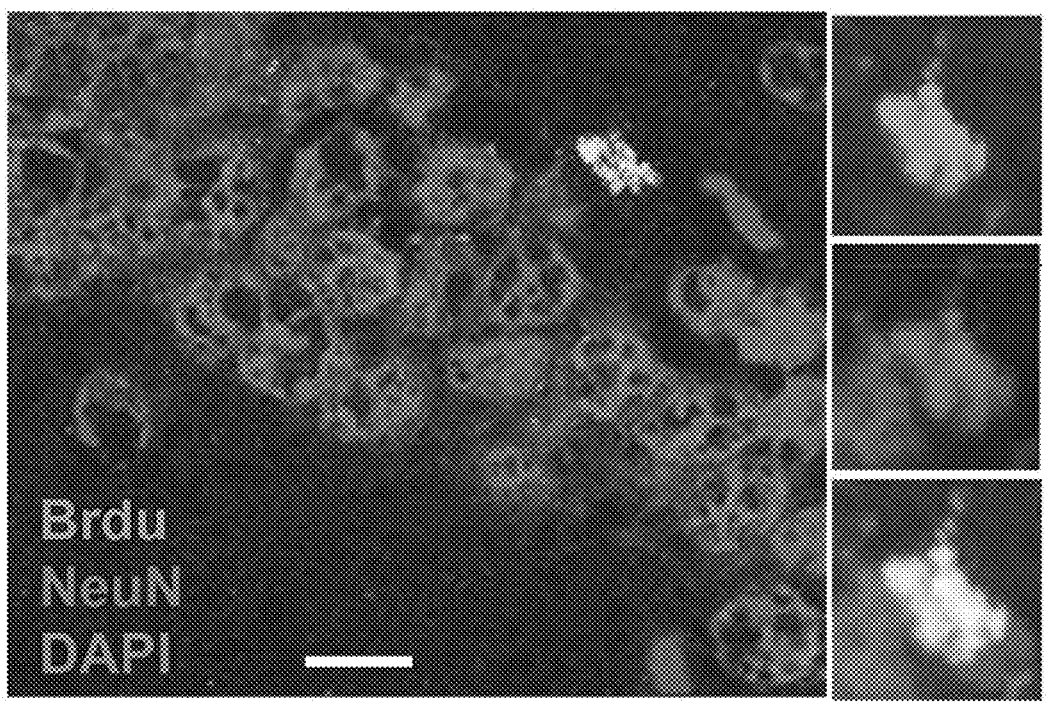
Figure 2C:
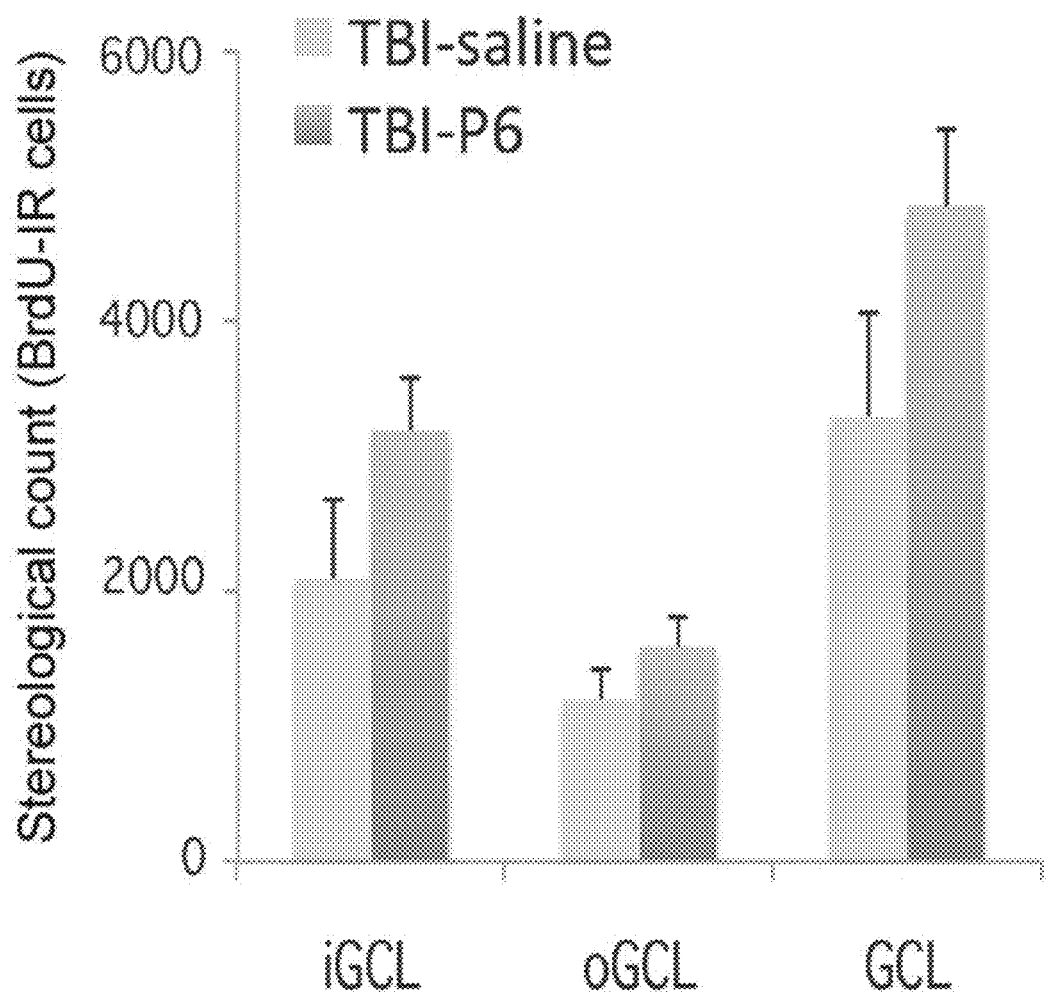
Figure 2D:
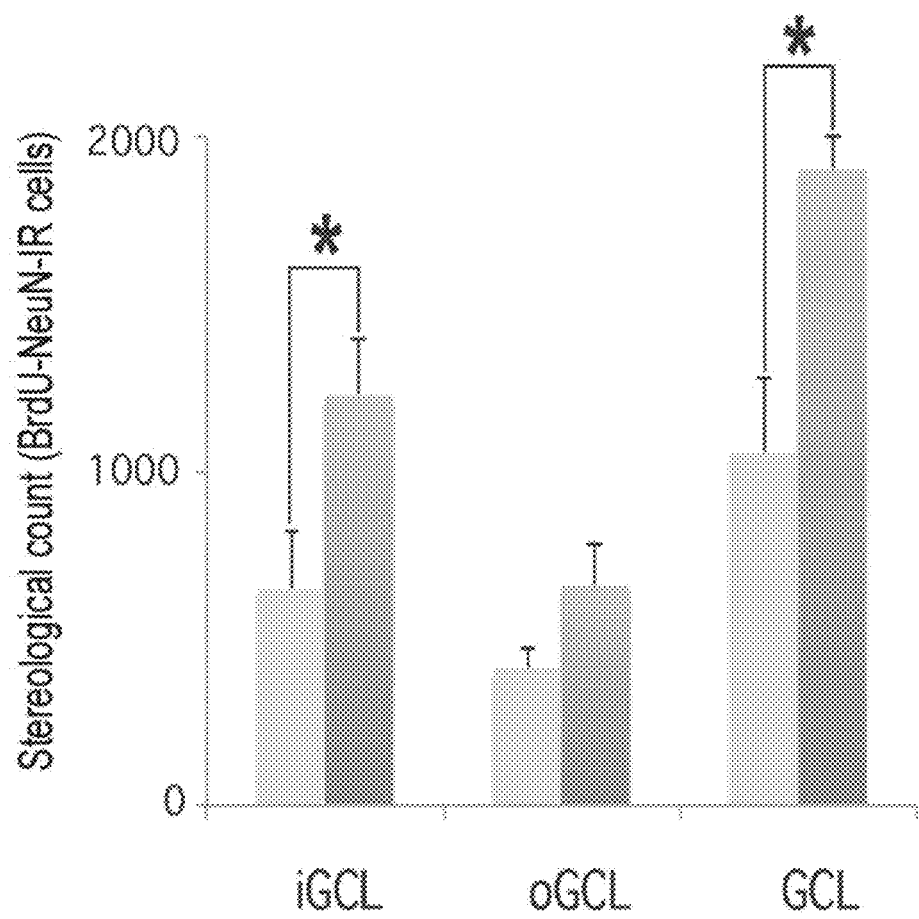
Figure 2E:
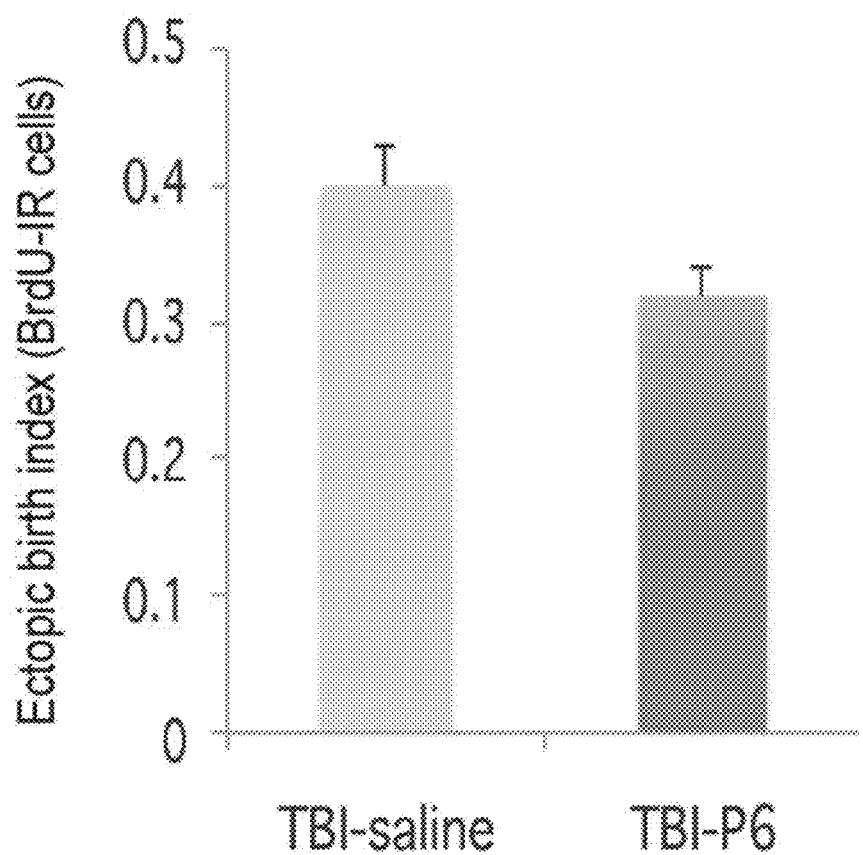
Figure 2F:
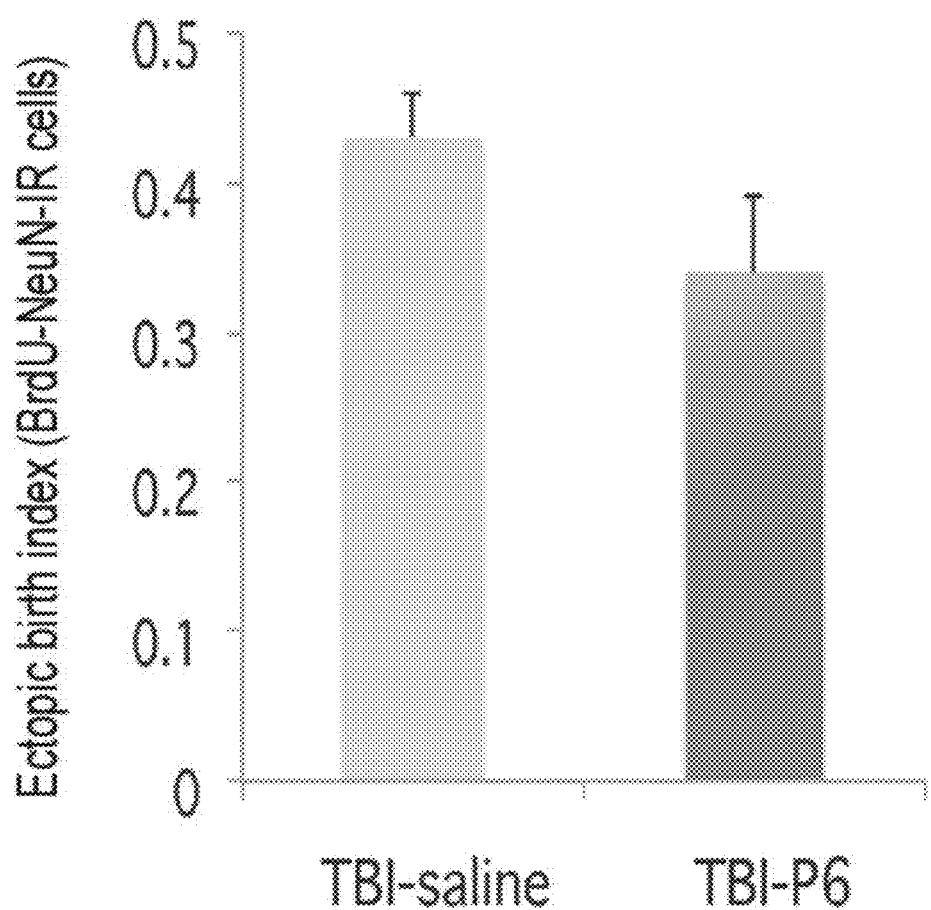

FIG. 2B is an image showing new born neurons in the granule cell layer of a TBI-Peptide 6 treated mouse. The right three panels show identity of a new born neuron (green: BrdU, red: NeuN, blue: DAPI). Scale bars in (A) and (B) are 100 μm and 10 μm, respectively;

FIG. 2C is a graph showing there was no statistical difference between the number of BrdU-IR cells in saline and Peptide-6 treated mice;

FIG. 2D is a graph showing chronic treatment with Peptide 6 significantly increased the number of newborn neurons (BrdU-NeuN-IR cells) in the dentate gyrus of TBI mice;

FIGS. 2E and 2F are graphs showing "Ectopic birth index" calculation suggested that up to 40% of newborn cells and 43% of newborn neurons were located beyond the iGCL of DG in TBI-saline mice suggesting "ectopic birth" and/or aberrant migration. Although not statistically significant, this number was lower in Peptide 6 treated group (32% and 34% respectively). BrdU (5'bromodeoxyuridine), BrdU-IR (BrdU immunoreactive), oGCL (outer granule cell layer), iGCL (inner granule cell layer), DG (dentate gyrus). Statistical analysis done using Student's t-test with p value <0.05 (*) "Ectopic birth index" calculations were performed using the formula (oGCL/GCL) according to Donovan et al.

Figure 3A:
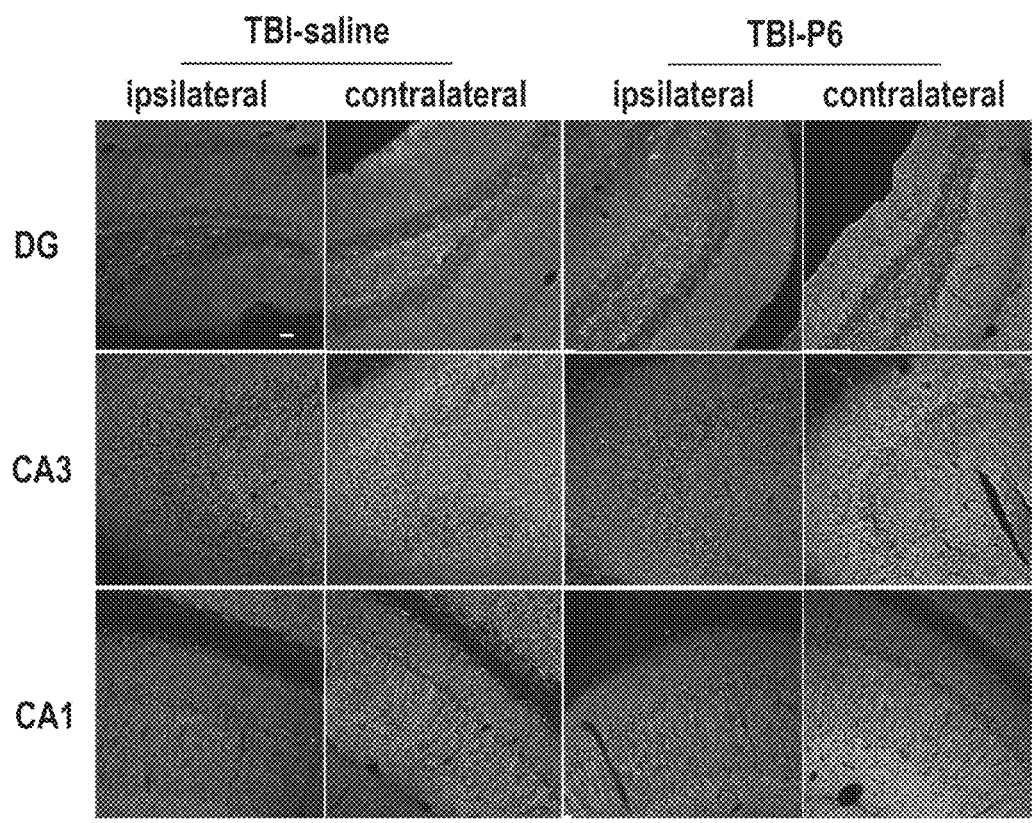
Figure 3B:
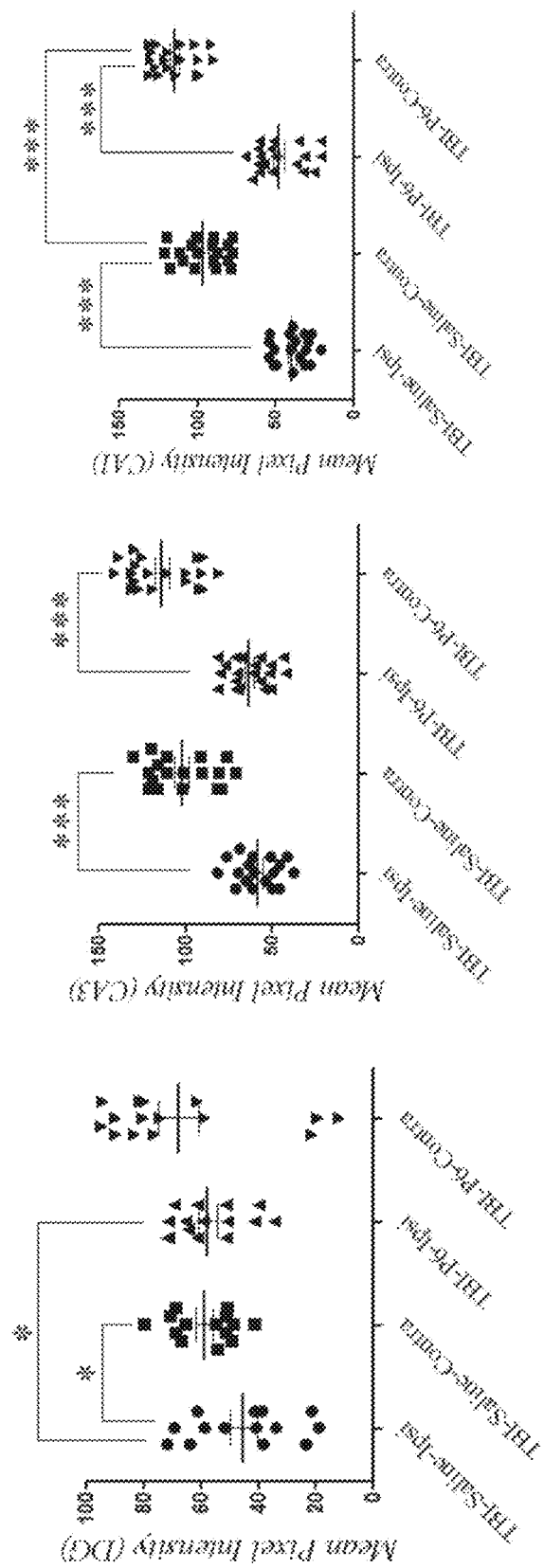

FIG. 3A is a series of photomicrographs illustrating MAP2 immunoreactivity in different areas of the hippocampus in saline and Peptide 6 treated TBI-mice where the scale bar=100 μm;

FIG. 3B is a series of graphs showing that there was a significant loss of dendritic density in the ipsilateral DG, CA3 and CA1 subregions of TBI-mice hippocampus compared to contralateral regions, with (B, left panel) showing chronic treatment with Peptide 6 increased MAP2 staining by 28% in DG ipsilateral to the injury as compared to saline treated mice. A similar, but non-significant, trend was also observed in CA3 (B, middle panel) and CA1 (C, right panel) regions in Peptide 6 treated mice. Scale bar=100 Jim. MAP2 (microtubule associated protein 2), TBI-P6 (TBI-Peptide 6 treated group) * ($p<0.05$), ($p<0.01$), *($p<0.001$), one way ANOVA, Bonferroni's post-hoc test or Student's t-test.

Figure 4A:
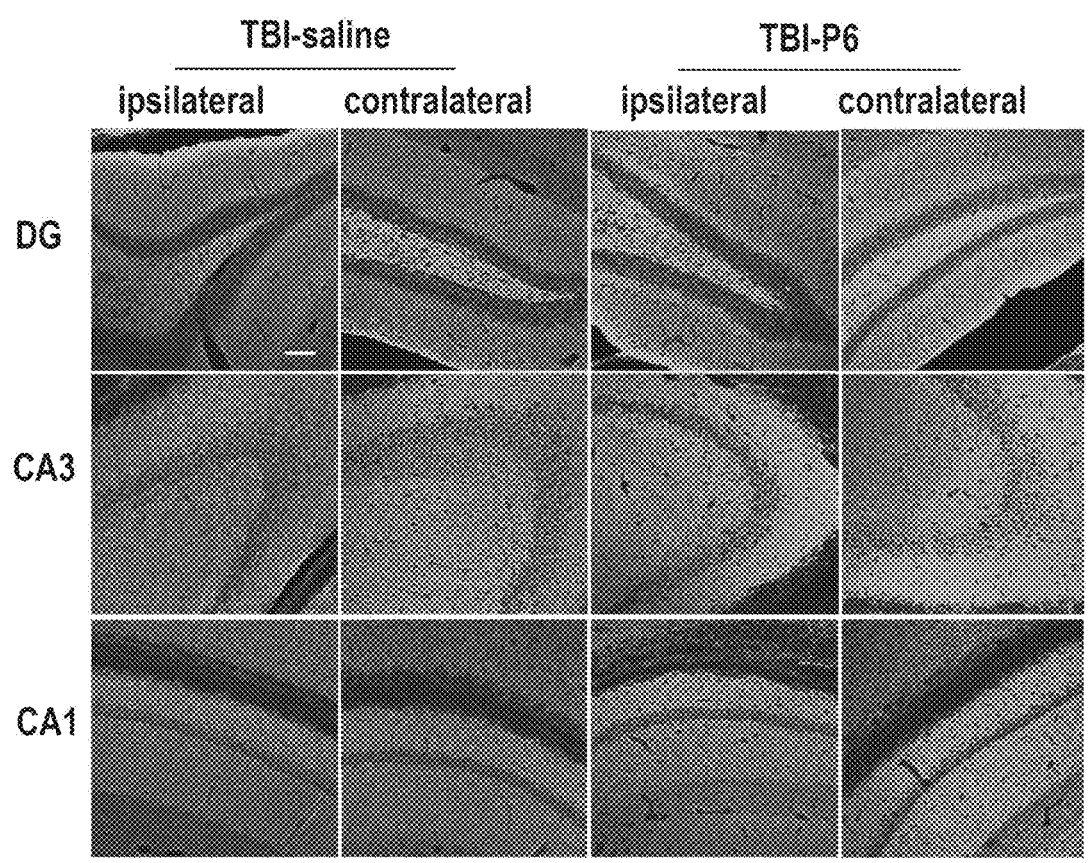
Figure 4B:
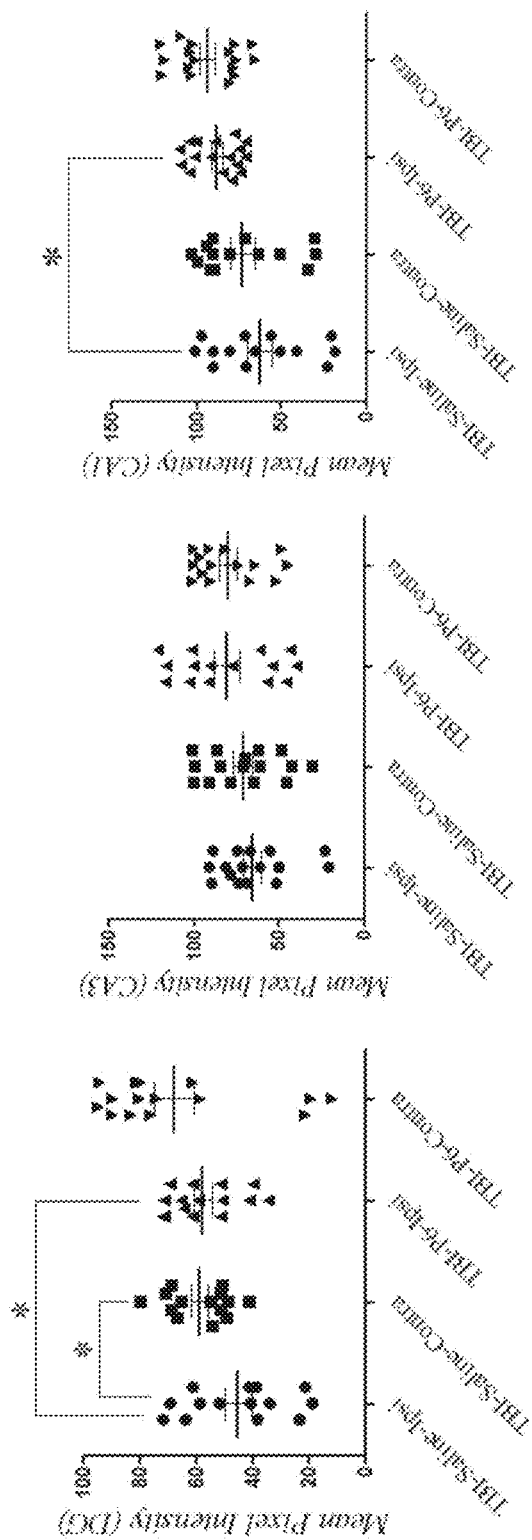

FIG. 4A is a series of photomicrographs illustrating synaptophysin immunoreactivity in different areas of the hippocampus in saline and Peptide 6 treated mice where the scale bar=100 μm;

FIG. 4B is a series of graphs showing that, compared to contralateral side, there was significant decrease in synaptophysin immunoreactivity in ipsilateral DG but not CA3 or CA1 regions of TBI-mice hippocampus. There was a 27%, 23% and 40% increase in synaptic density in DG (B, left panel), CA3 (B, middle panel) and CA1 (B, right panel) regions on the ipsilateral side in Peptide 6 treated TBI-mice as compared to saline treated animals. Scale bar=100 μm. DG (dentate gyrus), TBI-P6 (TBI-Peptide 6 treated group) * ($p<0.05$), one way ANOVA, Bonferroni's post-hoc test, or Student's t-test.

Figure 5A:
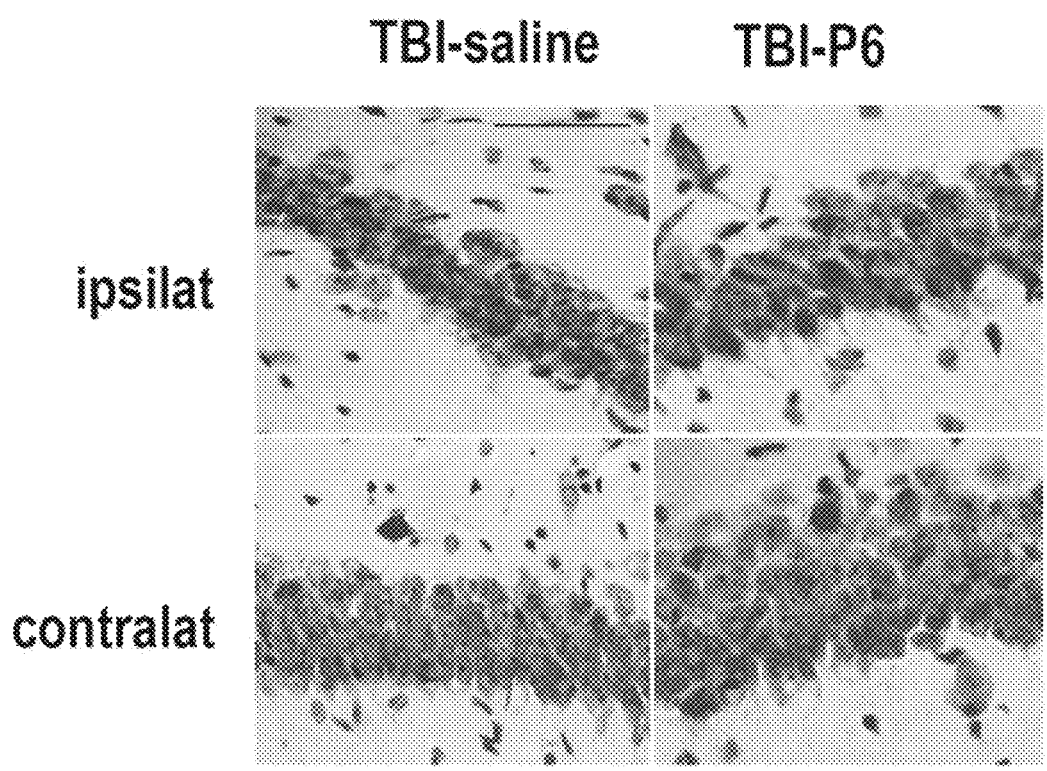
Figure 5B:
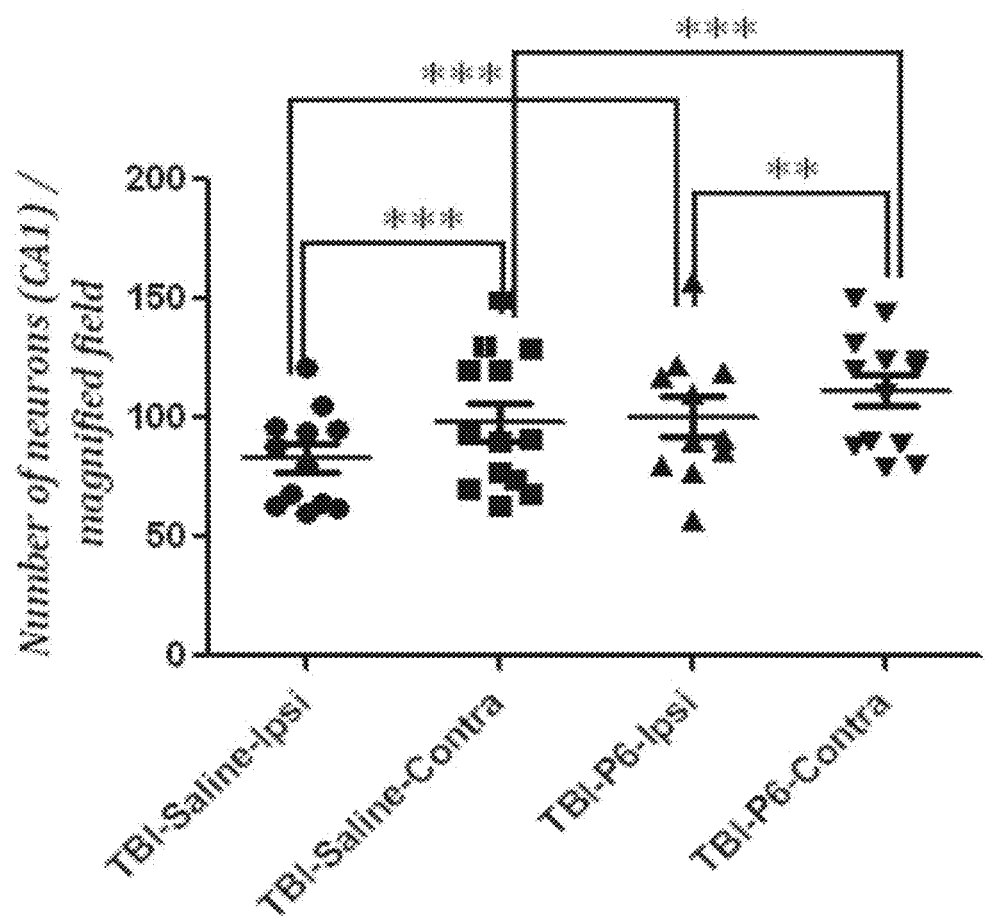
Figure 5C:
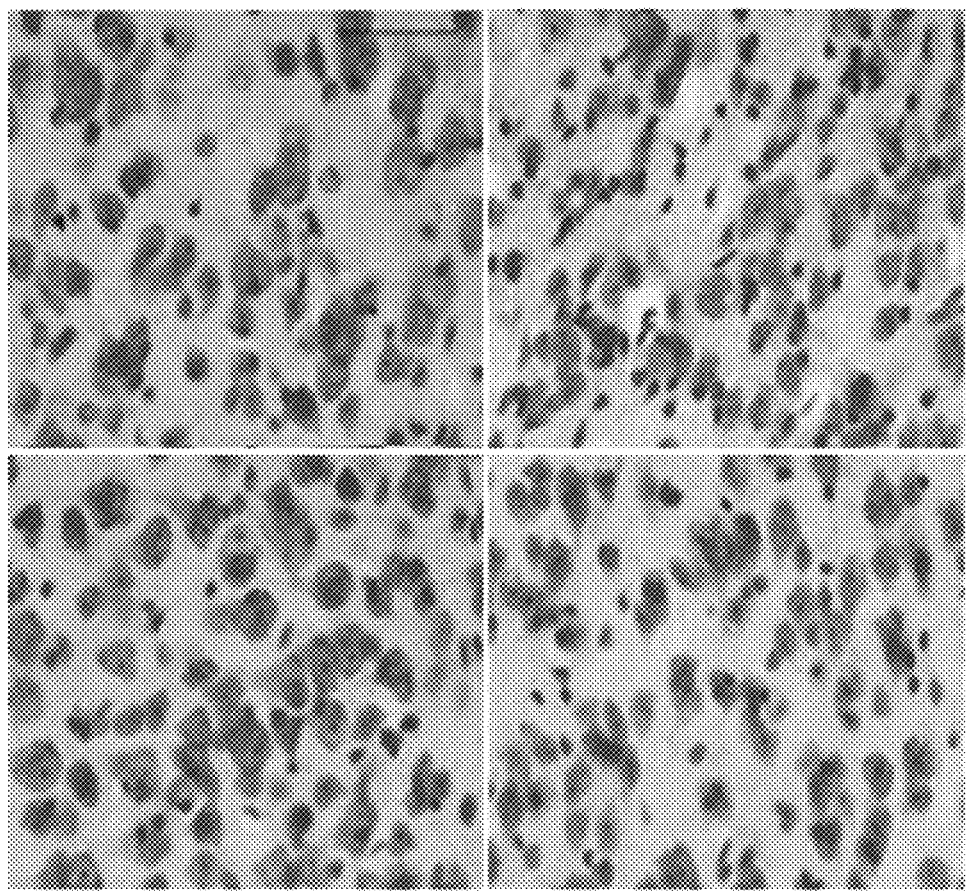

FIG. 5A is a series photomicrographs demonstrating Nissl staining in the CA1 region with scale bar=50 μm;

FIG. 5B is a graph showing significant loss of neurons in the ipsilateral CA1 region where chronic treatment with Peptide 6 prevented this loss;

FIG. 5C is a series of photomicrographs demonstrating Nissl staining in the parietal cortex with scale bar=50 μm.

Figure 5D:
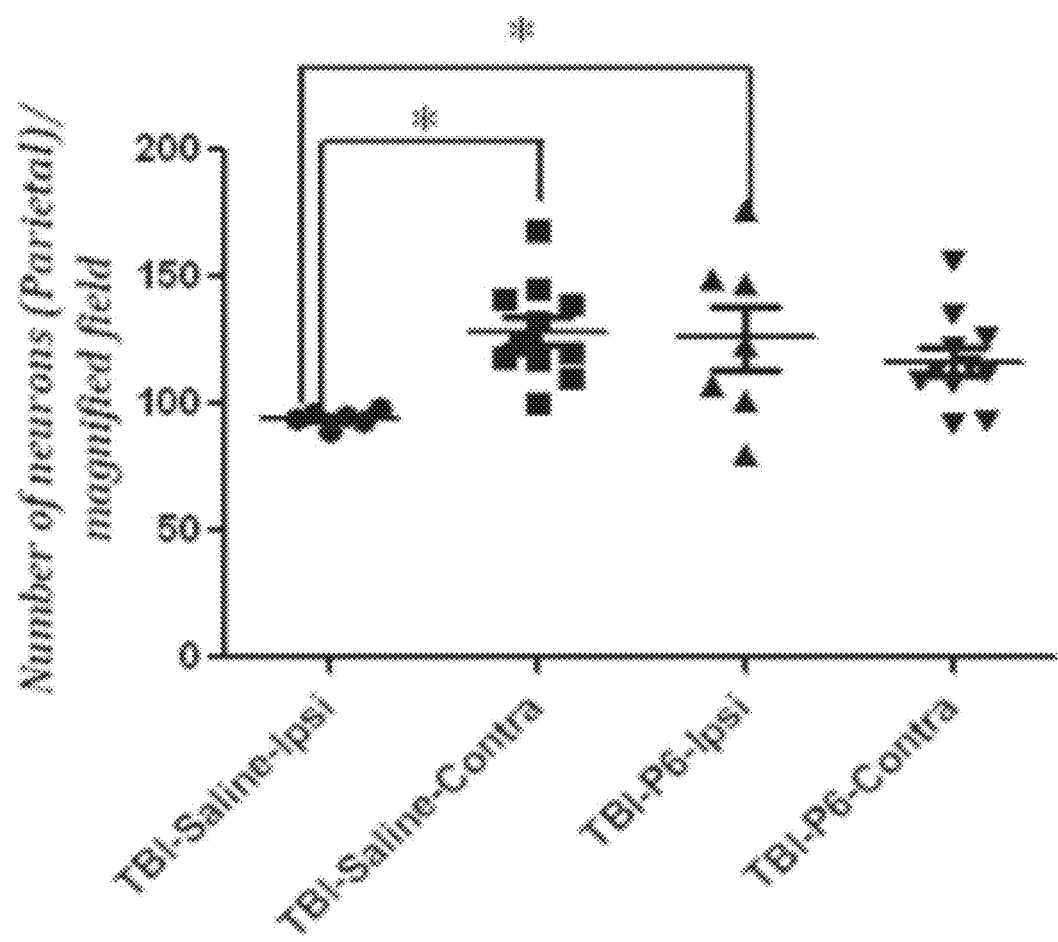
Figure 5E:
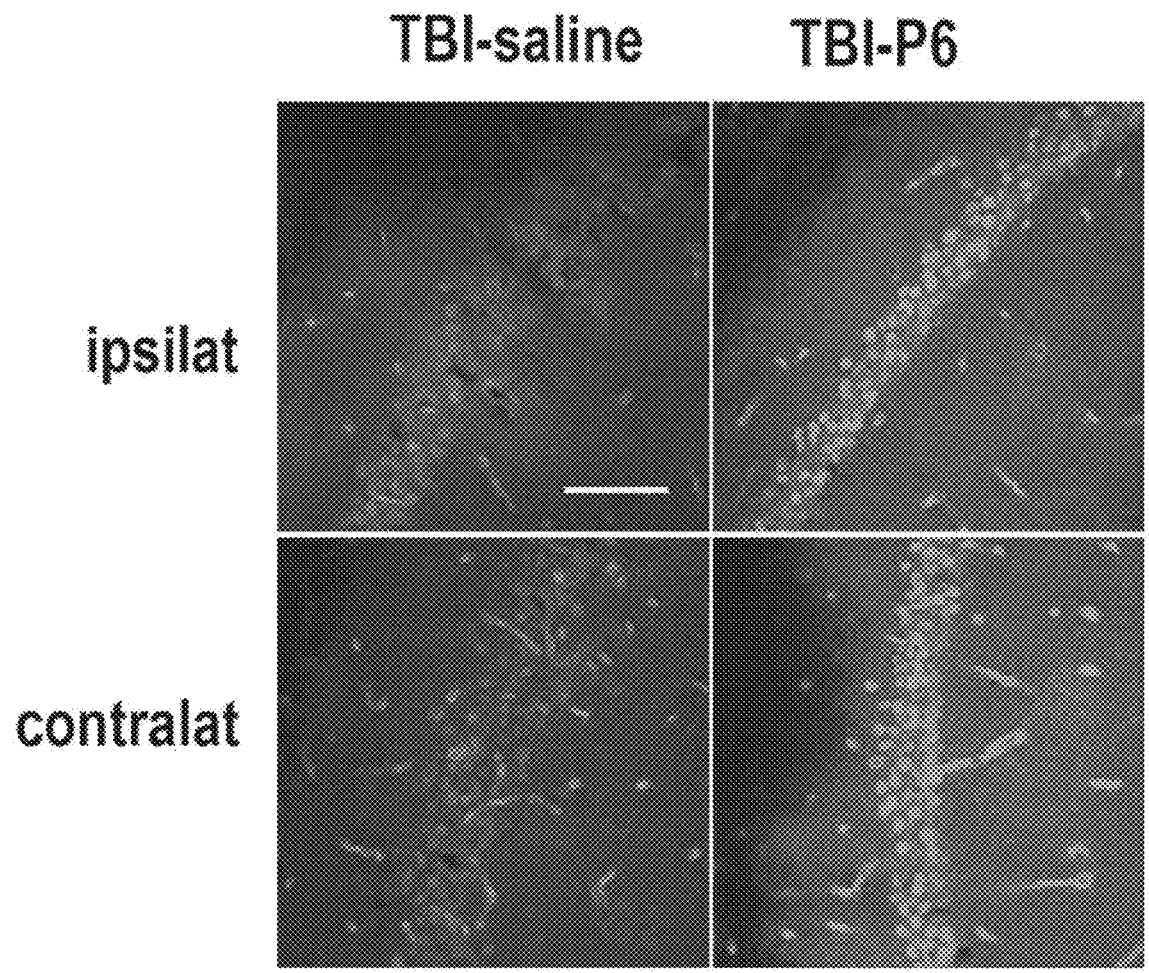
Figure 5F:
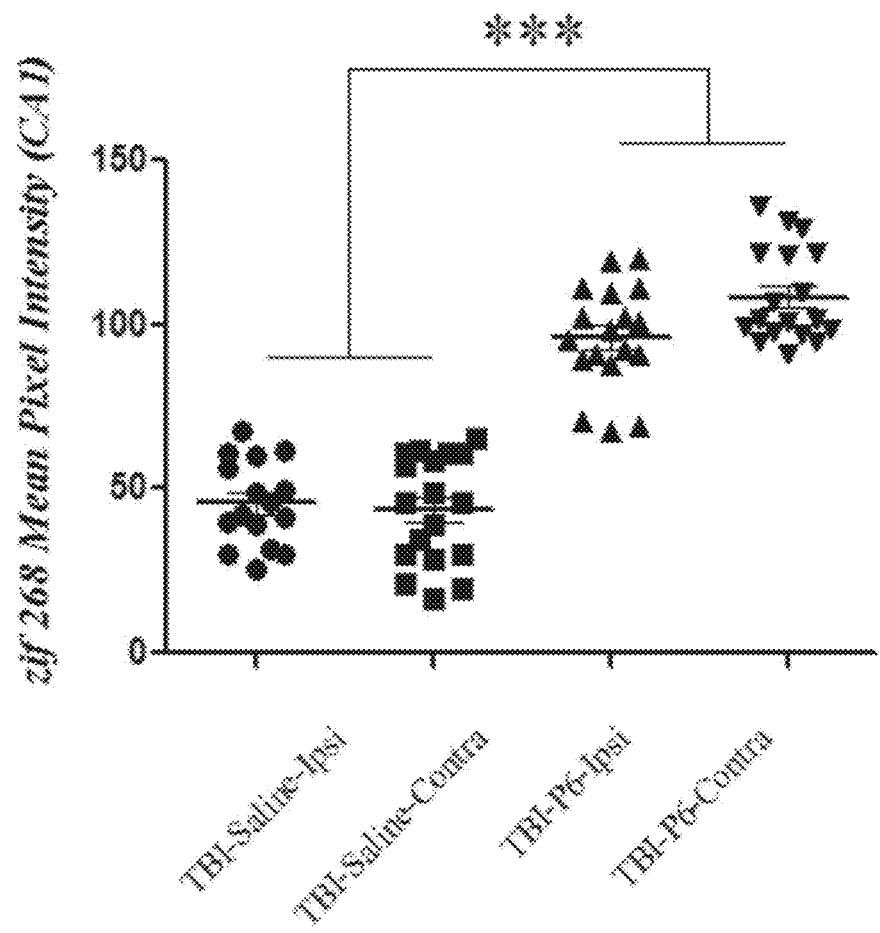
Figure 6A:
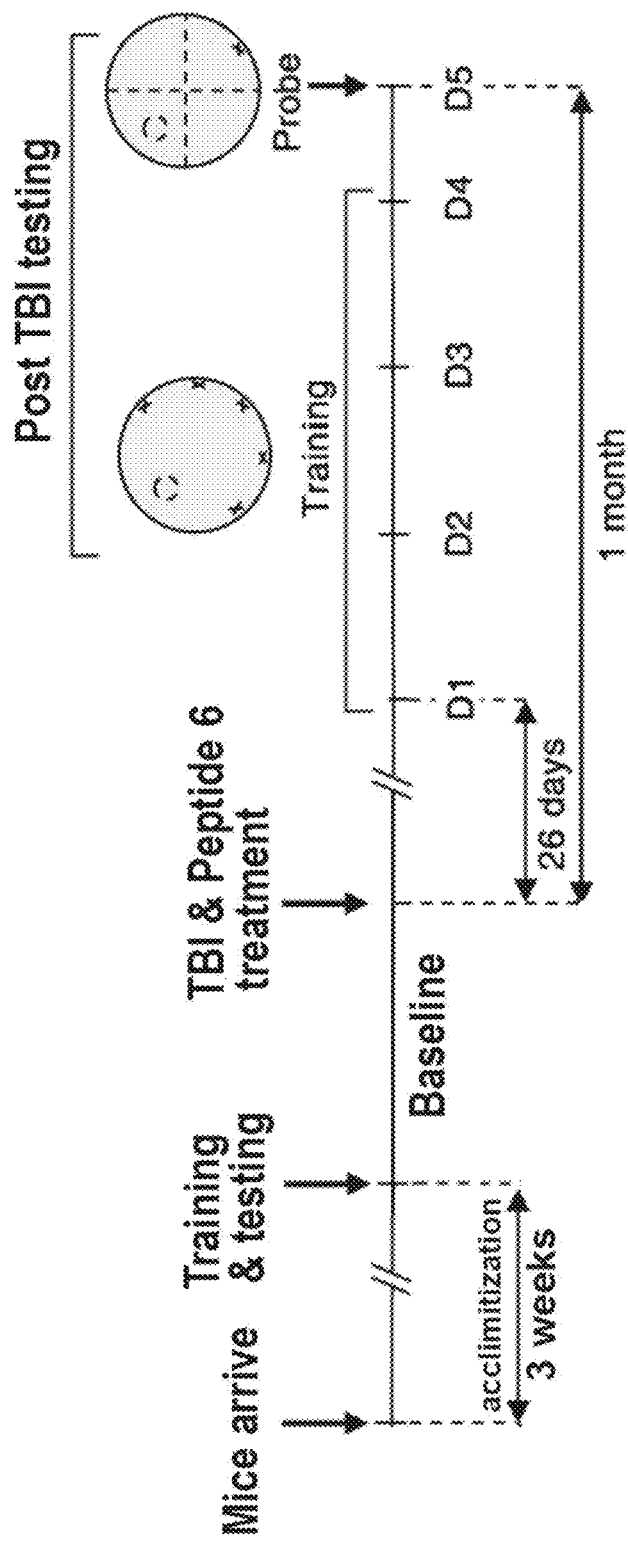
Figure 6B:
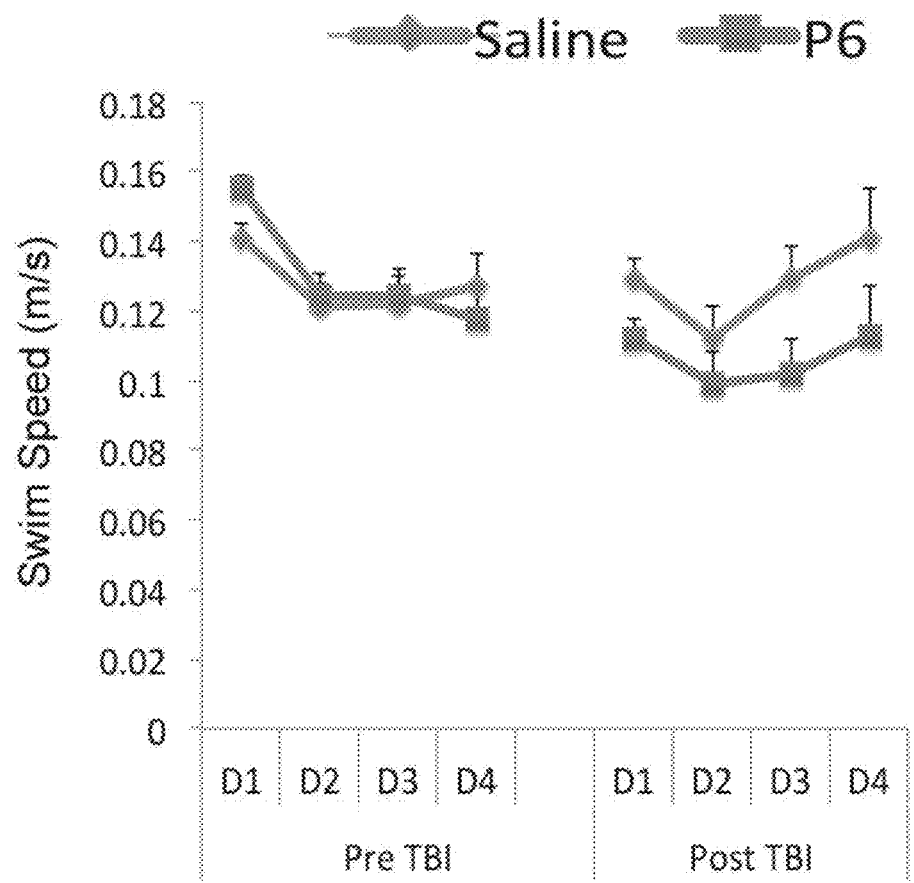
Figure 6C:
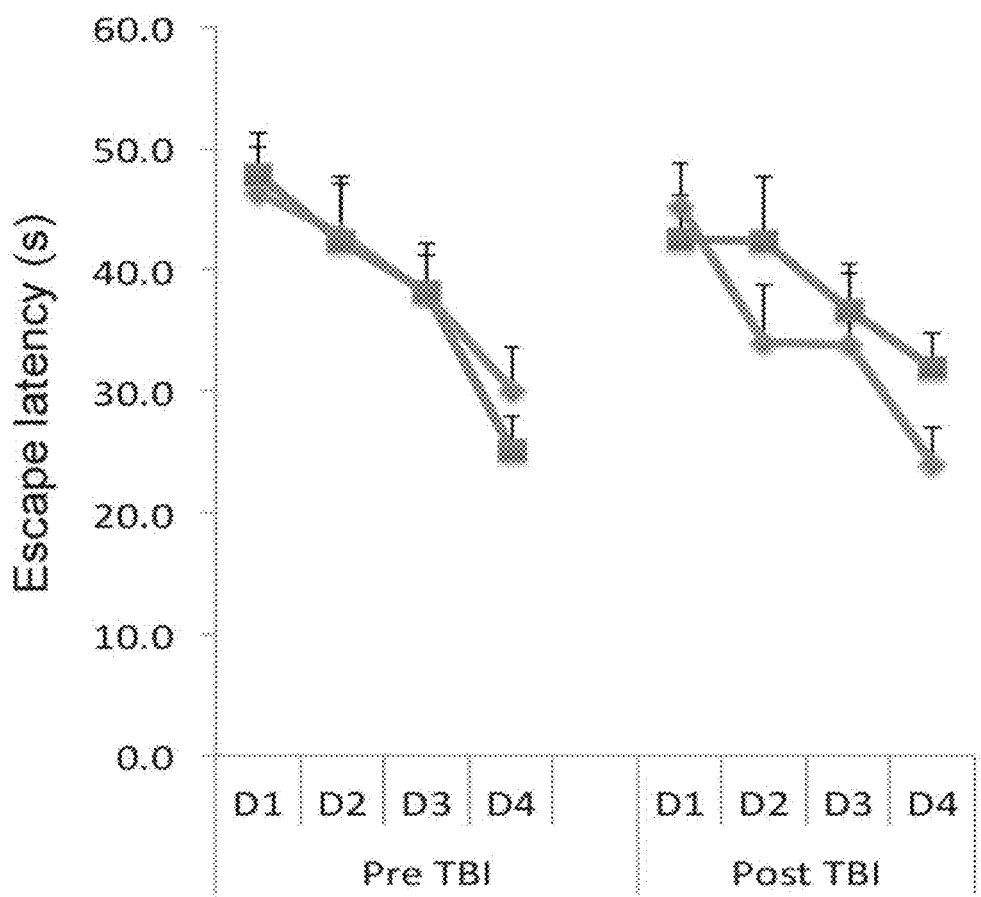
Figure 6D:
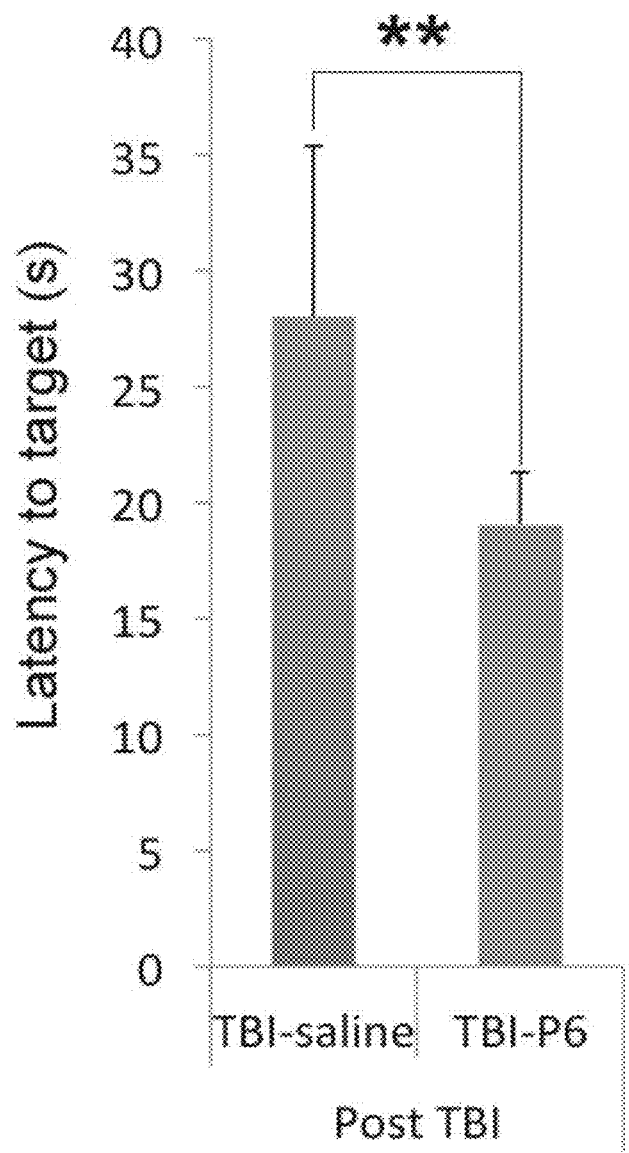
Figure 6E:
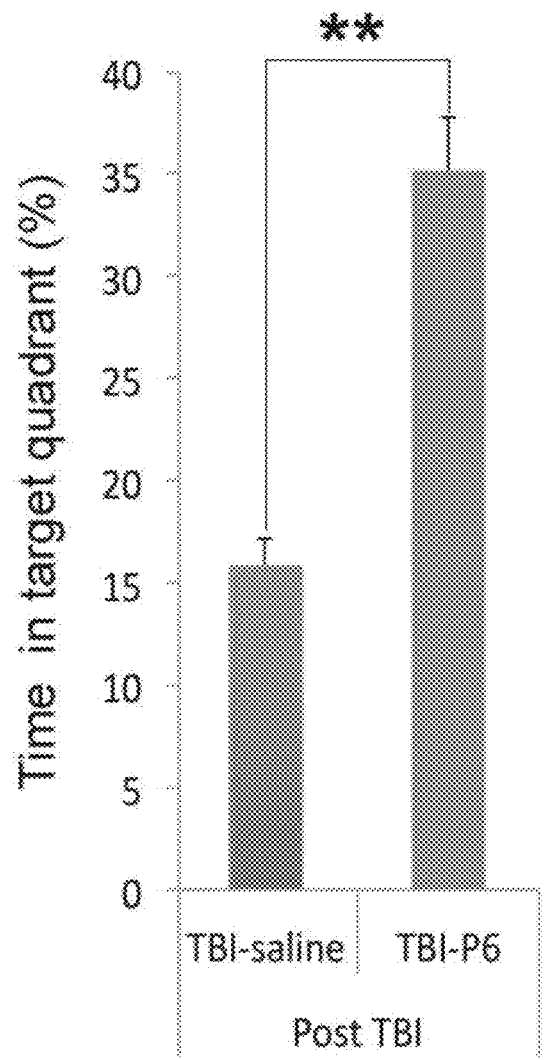
Figure 6F:
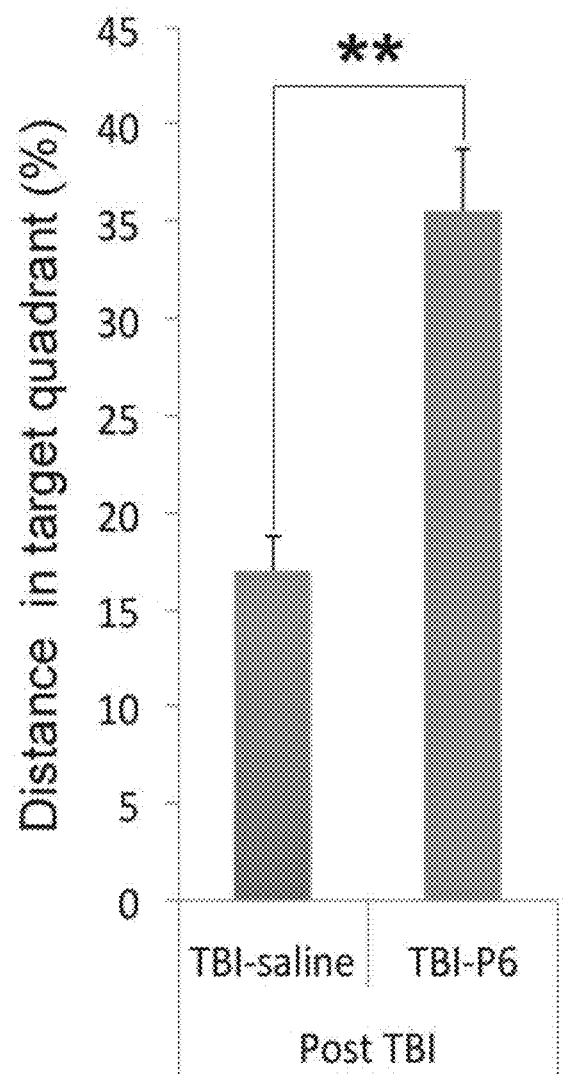

FIG. 5D is a graph showing significant loss of neurons in the parietal cortex where chronic treatment with Peptide 6 prevented this loss;

FIG. 5E is a series of photomicrographs with scale bar=100 μm illustrating immediate-early gene expression (zif 268) in the CA1 region of saline and Peptide 6 treated TBI-mice, 30 days after injury and within 3 hours of performance in a hippocampus-dependent memory task;

FIG. 5F is a graph showing that there was an almost 130% increase in the levels of zif268 in CA1 region of Peptide 6 treated TBI-mice as compared to saline treated animals in both ipsilateral and contralateral sides. TBI-P6 (TBI-Peptide 6 treated group) ***($p<0.001$), Student's t-test;

FIG. 6A is a graph showing the behavioral testing paradigm on Morris Water Maze (MWM). After 3 weeks of acclimatization, all animals underwent 4 day training on the MWM to establish baseline learning. The mice were retrained on day 26 after TBI and treatment (saline or Peptide 6) with the probe trial on day 30;

FIG. 6B is a graph showing there was no difference in pre or post TBI swim speeds between the various groups;

FIG. 6C is a graph showing that all animals showed equivalent learning on MWM as evidenced by decreasing escape latencies from day 1 to day 4 (repeated measures ANOVA). Additionally, there was no effect of Peptide 6 on learning in TBI animals D1 (day 1);

FIG. 6D is a graph showing that, on probe trial, Peptide 6 treatment caused significant improvement in latency to target, FIG. 6E is a graph showing percent time spent in target quadrant;

FIG. 6F is a graph showing percent distance covered in target quadrant. TBI-P6 (TBI-Peptide 6 treated group), ** ($p<0.01$) one-way ANOVA, post hoc Tukey.

Figure 7A:
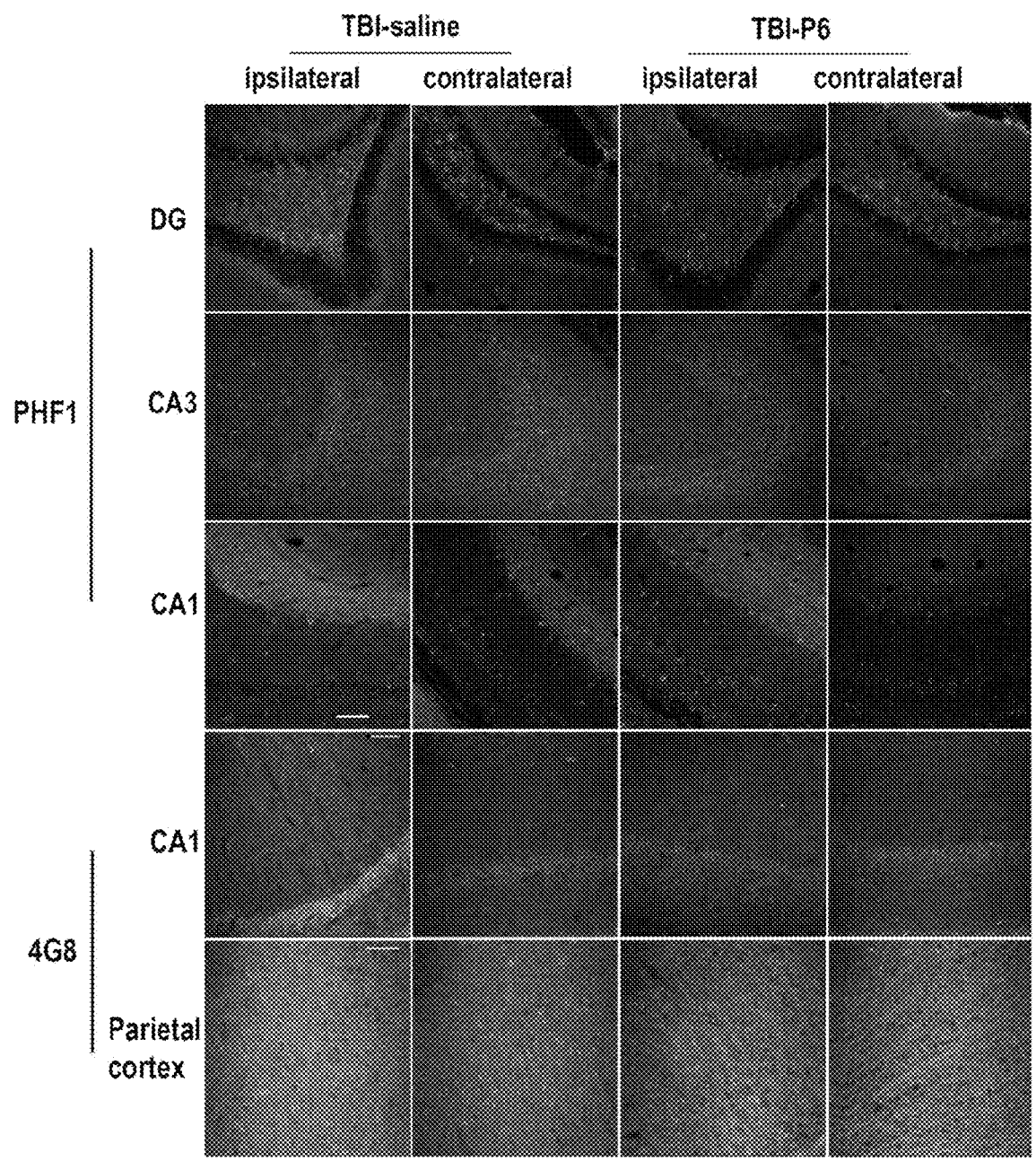
Figure 7B:
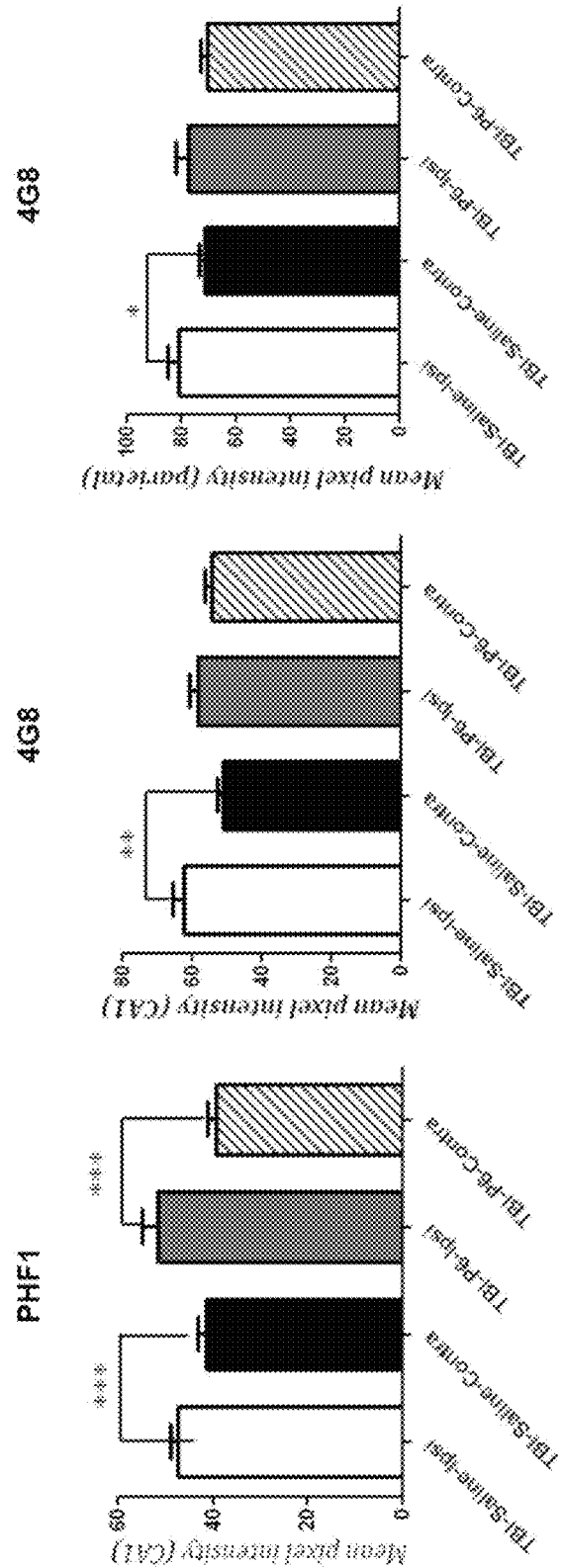

FIG. 7A is a series of images showing the elevation of Alzheimer-type biomarkers in TBI mice where immunohistochemical staining of hippocampus and parietal cortex revealed elevation of hyperphosphorylated tau and Aβ, two key hallmarks of Alzheimer disease in ipsilateral versus contralateral regions. Red: PHF1 staining against phosphor-tau at serine 396/404 (Scale bar=100 μm); Green: 4G8 staining against APP and Aβ (Scale bar=50 μm) *(p<0.05), (p<0.01), *(p<0.001), one way ANOVA, Bonferroni's post hoc test;

FIG. 7B is a series of graphs showing the elevation of Alzheimer-type biomarkers in TBI mice where immunohistochemical staining of hippocampus and parietal cortex revealed elevation of hyperphosphorylated tau and Aβ, two key hallmarks of Alzheimer disease in ipsilateral versus contralateral regions.

DETAILED DESCRIPTION OF THE INVENTION

The ciliary neurotrophic factor (CNTF) is a major determining factor for neurogenesis, both in hippocampus and subventricular zone. Like other neurotrophins, the therapeutic potential of exogenous CNTF is eclipsed by its short half-life when administered peripherally, requiring invasive mode of administration with unpredictable pharmacokinetics. In a mild-to-moderate TBI mouse model, the present invention shows that Peptide 6 enhances differentiation of newly born progenitors in the dentate gyrus 30 days after injury. This neurogenic effect of Peptide 6 may be due to its partial inhibition of leukemia inhibitory factor (LIF) activity by directly binding to the D1 cap region of LIF receptor. The fact that there was no statistical increase in the number of progenitors suggests a specific effect of Peptide 6 in promoting neuronal maturation and survival that is not seen naturally after TBI. Importantly, the newborn mature neurons remain within the physiological confines of the GCL and display no ectopic migration or birth, a phenomenon linked with epilepsy and schizophrenia. A robust correction of dendritic and synaptic markers was seen in key regions of the injured hippocampus shows that Peptide 6 provides a neurotrophic milieu that can help sustain local microenvironment after mild-to-moderate brain injury.

As explained in U.S. patent application Ser. Nos. 13/676,649, 13/044,323, and 12/531,616, certain fragments of Peptide 6 may provide the same functionality as the entire sequence and thus are encompassed by the present invention. Similarly, the present invention also encompasses capping of Peptide 6, or fragments of Peptide 6, such as with adamantylated amino acid. For example, capping the N-terminus of the sequence of Peptide 6c with adamantane-1-carboxylic acid, has been shown to further increase lipophilicity and BBB penetration as well as resistance against aminopeptidase activity. The adamantyl group may be selected from the group consisting of adamantyl-L-glycine, adamantyl-L-alanine, alkylated adamantane groups, isomers of adamantanes and di- or triadamantane groups.

EXAMPLE 1

Generation of Peptide 6:

Peptide 6 was generated based on epitope mapping of neutralizing antibodies to human CNTF (Pepscan, Lelystad, The Netherlands), which resulted in an 11-mer peptide, Peptide 6, VGDGGLFEKKL (SEQ ID NO: 1), which is both neurogenic and neurotrophic, as set forth in U.S. patent application Ser. Nos. 13/676,649, 13/044,323, and 12/531,616, as well as PCT/EP2008/002106, and European Application No. 07450050.5, all of which are hereby incorporated by reference in their entireties. Peptide 6, which comprises residues 146-156 of human CNTF, may be synthesized by solid phase peptide synthesis (SPPS) methods, purified by reversed phase HPLC to greater than 96 percent purity, lyophilized, and characterized via HPLC, NMR, and ESI-MS Antibodies:

The following primary antibodies were used for immunohistochemistry (IHC): anti-BrdU (1:400; Accurate, Westbury, N.Y.), anti-NeuN (1:500; Chemicon, Temecula, Calif.), SMI52 (anti-MAP2; 1:1000, Cavance, Calif.), anti-synaptophysin (1:200; Millipore, Temecula, Calif.), Egr-1 (anti-zif 268; 1:100, Santa Cruz Biotechnology, Santa Cruz, Calif.), 4G8 (anti-Aβ; 1:200; in-house) and PHF1 (monoclonal antibody to phosphorylated tau at serine 396 and serine 404; 1:200; a gift from Dr. Peter Davies, Albert Einstein College of Medicine). The following secondary antibodies were used: Alexa 488 conjugated goat anti-mouse IgG and Alexa 594 conjugated goat anti-rabbit or anti-rat IgG (Molecular Probes, Carlsbad, Calif., USA). Nuclear staining was obtained using DAPI (Sigma-Aldrich, St. Louis, Mo.).

Animals and Housing:

All in vivo studies were performed on 3-4-month-old female mice of C57BL6 strain) with a 12:12 light: dark cycle, with free access to food and water and were given a period of acclimatization before any studies were performed. The studies were conducted under protocol #100954 of the Institutional Animal Care and Use Committee of the University of New Mexico.

Induction of TBI in Mice:

Induction of TBI in mice was based on a known CCI model. Briefly, mice were anesthetized with isoflurane (5% induction, 2% maintenance with 70% nitrous oxide and 30% oxygen) and placed in a stereotaxic frame. After a midline skin incision, a 5 mm left lateral craniotomy was made using a motorized drill. CCI was induced with an impact device using a 3 mm diameter metal tip with a velocity of 5 m/sec to a penetration depth of 1.5 mm below the dura. The impact was centered at 2.7 mm lateral to midline and 3.0 mm anterior to lambda. The craniotomy site was sealed with Loctite Gel glue (Henkel Corp., Rocky Hill, Conn.) and the scalp was sutured. The mice were given antibiotic prophylaxis with 500 units/gm of IM Bicillin (Pfizer, N.Y.) peri-operatively and 0.01 mg/kg twice daily of buprenorphine (Reckitt Benckiser Pharmaceuticals, N Chesterfield, Va.) for three days for comfort.

Figure 1A:
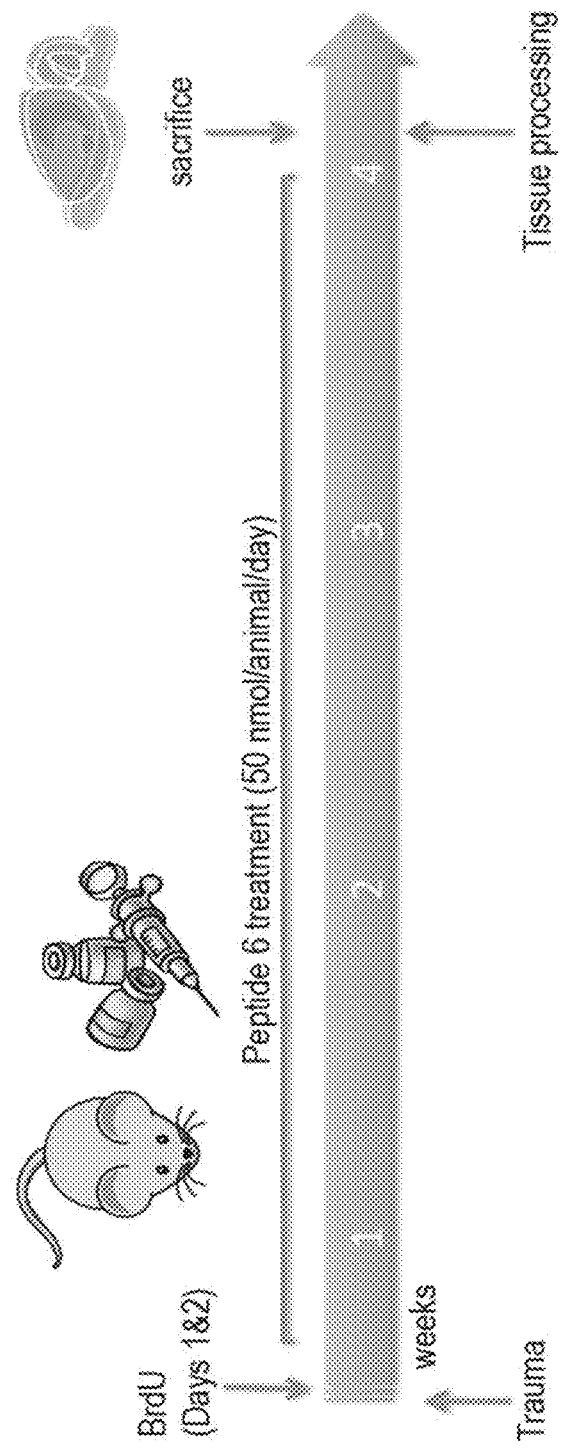
FIG. 1E is a Nissl staining depicting typical cytoarchitectural changes in the TBI-mouse 30 days after injury (10× magnification).
Figure 1B:
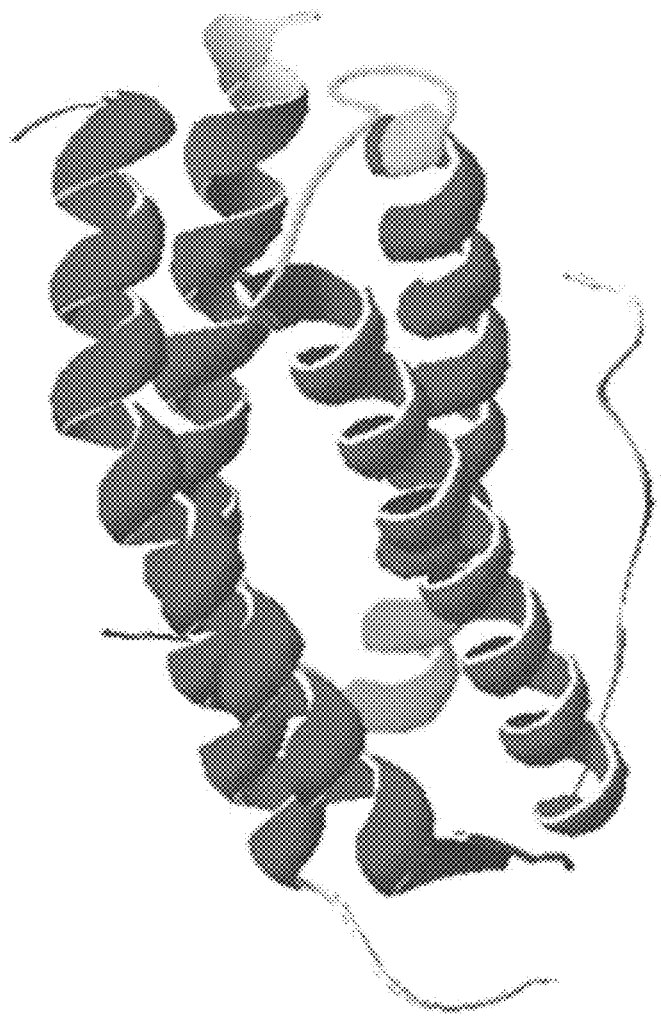

Administration of BrdU and Peptide 6:

To study neurogenesis, animals were given intraperitoneal (i.p.) injections of Peptide 6 (50 nmol/animal/day) or saline (control) for 30 days. Mice in either treatment group received twice-daily injections of BrdU (75 mg/kg, Sigma-Aldrich, St. Louis, Mo.) for two days beginning one-day post trauma (FIG. 1A).

Tissue Processing and Immunohistochemistry (IHC):

Tissue processing and IHC was performed. Briefly, mice were anesthetized with pentobarbital (125 mg/kg) and transcardially perfused with 0.1M phosphate buffered saline (PBS) followed by 4% paraformaldehyde (PFA). The brains were then kept in 4% PFA solution for 24 hours and stored in 30% sucrose solution at 4° C. till further use. Coronal sections (35 μm) were obtained on a freezing sliding microtome and stored in glycol anti-freeze solution (ethylene glycol, glycerol and 0.1M PBS in 3:3:4 ratio) at −22° C. until further use. IHC was performed on free-floating sections. Every 5th brain section was chosen for cell counts and every 10th section for immunoreactivity quantification using uniform random sampling.

Stereology & Confocal Microscopy:

Neurogenesis was assessed in the DG by counting the number of BrdU-immunoreactive (BrdU-IR) and BrdU-NeuN-IR cells in various layers of the DG. The granule cell layer (GCL) was further subdivided into an inner and out half (iGCL and oGCL) as described previously. To assess cell proliferation, Brdu-IR cells were counted in every 5th section using a 40× oil objective of a Nikon 90i fluorescent microscope equipped with a Nikon C1 3-laser confocal system. Employing principles of unbiased stereology, the optical fractionator method was used to estimate cell counts for the DG5. For each brain, at least 100 cells were counted based on coefficient of error determinations. To assess neuronal maturation, BrdU-NeuN-IR cells were counted using 100× oil objective in every 10th section. To ensure objectivity, z-stacks were collected for each double IR cell and analyzed later by generating maximum projection and 3D constructs. A cell was counted only when it showed double IR on 3D reconstructed images.

For MAP2, synaptophysin, zif268, PHF1 and 4G8-IR, the entire area of GCL, CA3 and CA1 was outlined on every 10th section at 20× magnification and maximum projection images were created based on confocal z-stacks using Nikon 90i fluorescent microscope equipped with Nikon C1 three-laser confocal system and a Nikon DS U1 digital camera. A mean pixel intensity (MPI) was recorded for each anatomical area using Image-Pro Plus 5.0 software (Media Cybernetics, Silver Spring, Md.).

MRI Acquisition:

MRI was performed on a 4.7 Tesla dedicated research MR scanner (Bruker Biospin, Ettlingen, Germany), equipped with a small-bore linear radiofrequency coil (72 mm). All data processing was performed using in-house developed software written in 64-bit MATLAB (Mathworks, Natick, Mass., USA) running on a UNIX machine. Initial localizer images were acquired followed by T2-weighted (T2WI) and diffusion-weighted images.

Behavioral Testing:

Behavioral testing included spatial reference memory test in the Morris Water Maze (MWM).

Spatial Reference Memory Task:

The test used is an adaptation of the Morris Water Maze test. The procedure was performed in a 180 cm diameter circular tank. The pool was filled with water (21° C.±1) made opaque by adding non-toxic white paint (RichArt, Northvale, N.J.). The maze had visual cues on all sides for spatial orientation. A digital camera with 40× optical zoom was mounted ~6 feet above the top of the maze to capture video. The escape platform was transparent measuring 4×4 inches and submerged ~1 cm below the water line. Ceiling mounted, fluorescent bulbs provided room lighting. All animals were first acclimated to the behavioral testing room before training was started. The test was performed over two phases on 2 groups of mice (11-12 mice each). The first phase was done on uninjured and untreated animals to establish baselines. Second phase was done 26 days after TBI and while treatment (saline or Peptide 6) was in its final week (FIG. 6A). All mice were trained for 4 days and given 4 trials per animal. During each trial, the mice were released randomly from the N, S, E or W side of the pool. They were given 60 seconds per trial to find the submerged platform. At the end of each trial the animals were left on the platform for 20 s then dried and returned to their home cage until the next trial. A test for retention (i.e. a probe trial, PT) was given 24 h after the last day of training. During the PT mice were allowed to swim in the tank without the escape platform for 60 seconds. The measures of learning were the time and the distance swum to reach the escape platform. For PT, the tank was divided into 4 imaginary quadrants and a small zone where the escape platform had been (i.e. target quadrant). The measures of memory on the PT were percent of time spent and percent of distance covered in the target quadrant. On day 27 after TBI induction, the mice were retrained as above and a probe trial performed on day 30 coinciding with the final day of treatment. All analyses were performed on ANY-MAZE software (Stoelting Co., Wood Dale, Ill.).

Figure 1C:
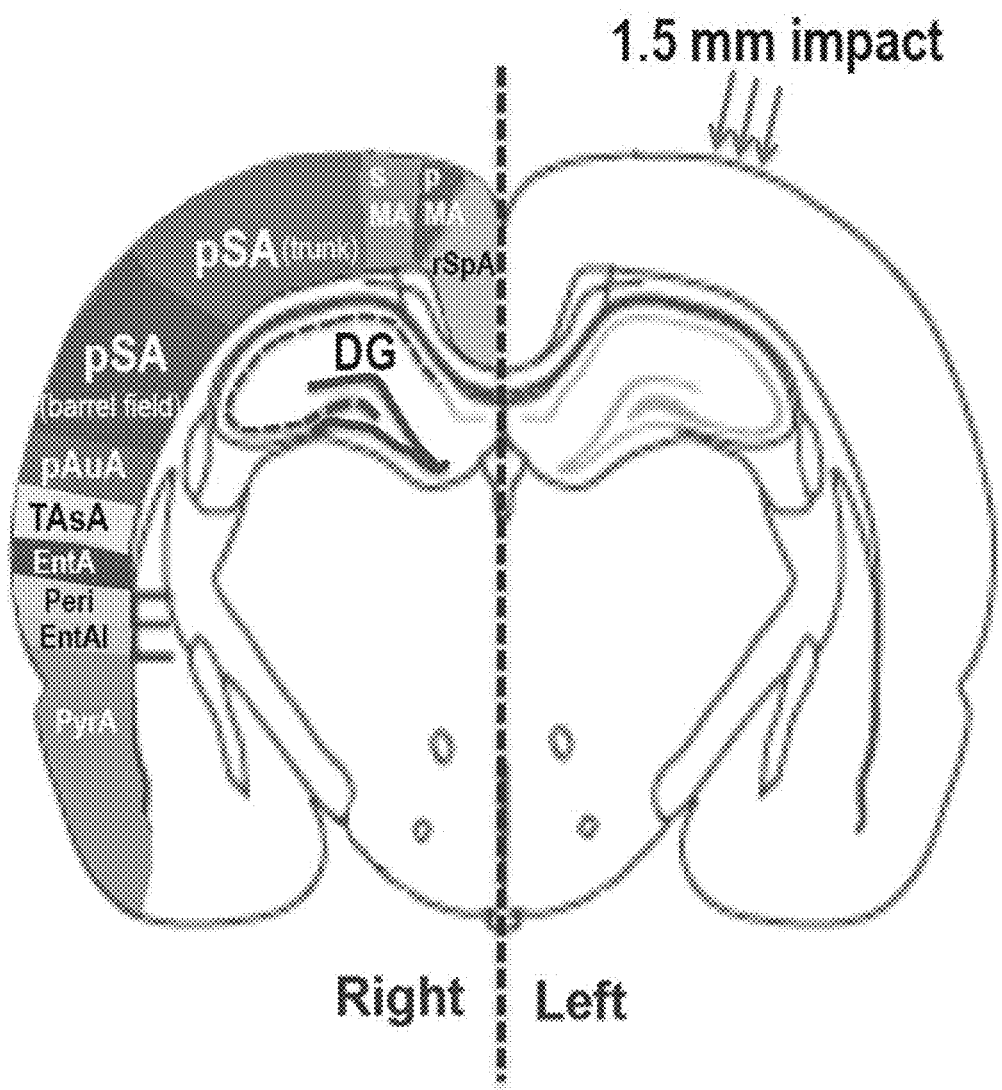
Figure 1D:
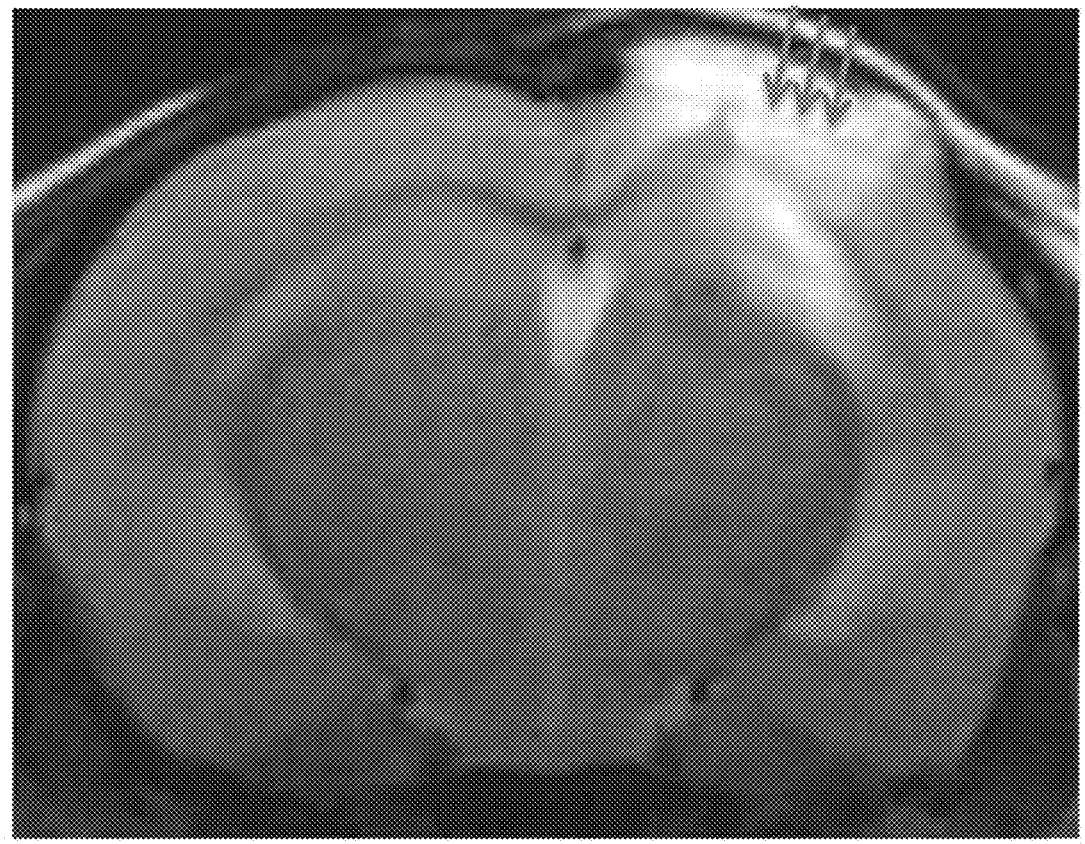
Figure 1E:

Statistics:

Data are presented as mean with standard error of mean (SEM). Kolmogorov-Smirnov test was used to determine normality of the data. For stereological studies an unpaired Student's t-test was used. For immunohistochemical analysis involving multiple groups, ANOVA with post hoc Bonferroni's test was used. Further intergroup comparisons involving the effect of TBI and/or treatment were performed using unpaired Student's t-test. For behavioral studies, either one-way or repeated measures ANOVA tests were used with post hoc Tukey or Bonferroni tests where appropriate. Statistical outliers were detected using Grubbs test for normally distributed data. Differences with $p<0.05$ were considered significant Anatomical Extent of Brain Injury in TBI-Mice:

Imaging studies performed 6 weeks after induction of TBI revealed extent of structural damage to the brain. Although the depth of brain deformation was kept at 1.5 mm, T2W MRI showed involvement beyond the contusion, including hippocampus and its subregions: DG, CA1 and CA3 regions (FIG. 1C-D). Nissl staining revealed a smaller and shrunk ipsilateral hippocampus compared to contralateral side (FIGS. 1E and 5A). There was obvious shrinkage of ipsilateral parietal somatosensory cortex on Nissl staining (FIGS. 1E and 5C). Although MRI T2 signal abnormalities extended medially into the secondary, and possibly, primary motor area, there was no evidence of gross motor abnormality on swimming speeds between the injured and sham groups (FIG. 6B).

Proliferation of Neural Progenitors in TBI-Mice Treated with Peptide 6:

There was no significant change in the number of BrdU immunoreactive (BrdU-IR) cells in the granule cell layer (GCL) of DG on chronic administration of Peptide 6 following trauma (FIG. 2B). Although stereological analysis of the number of progenitors in sub-regions of the DG revealed an increase in the number of BrdU-IR cells in the subgranular zone (SGZ) in Peptide 6 treated animals when compared to the saline control group (FIG. 2C and Table 1), this did not reach statistical significance (mean±SEM: 3303±765 control, 4850±568 Peptide 6, p=0.11, Student's t-test).

Similarly, stereological counts did not reveal any significant increase of BrdU-IR in the inner GCL (iGCL) of TBI-mice treated with Peptide 6 when compared to saline (3197±380 versus 2100±595, p=0.11, Student's t-test) or outer GCL (oGCL, 1203±220 versus 1588±224, p=0.25, Student's t-test; FIGS. 2 C and E, Table 1 below). Together, these data suggest that Peptide 6 did not increase neural progenitor cell proliferation in the GCL of DG.

TABLE 1

Stereological counts (mean ± SEM) of newborn progenitors (BrdU-IR cells) in various layers of the dentate gyrus.

|  | TBI-saline | TBI-Peptide 6 | p value |
| --- | --- | --- | --- |
| GCL | 3303(765) | 4850(568) | 0.11 |
| iGCL | 2100(595) | 3197(380) | 0.11 |
| oGCL | 1203(220) | 1588(224) | 0.25 |
| EBI (OGCL/GCL) | 0.40(0.03) | 0.32(0.02) | 0.08 |

Where GCL: granule cell layer, iGCL: inner granule cell layer, oGCL: outer granule cell layer, EBI: ectopic birth index, p-value based on unpaired Student's t-test.

Neuronal Differentiation of Progenitor Cells in the Dentate Gyrus:

More than half of newly born progenitors die before maturation (a process that takes at least three weeks); net neurogenesis in the DG is, therefore, determined by the number of progenitors that survive as mature neurons. In order to determine whether Peptide 6 induced differentiation of DG progenitors into mature neurons, the number of BrdU-IR cells expressing the mature neuronal marker NeuN in the GCL of the DG were counted, i.e. Brdu-NeuN-IR cells after 30 days of injury (FIG. 2D and Table 2 below). An 80% increase was found in BrdU-NeuN-IR cells in Peptide 6 treated TBI-mice when compared with the saline control group (mean±SEM: 1901±265 versus 1057±217, p=0.036, Student's t-test; FIG. 2D and Table 2). Sub region analysis of GCL again revealed focal and specific increase in treatment induced newborn neurons in the iGCL (1225±169 versus 648±176, p=0.03, Student's t-test) but not in oGCL(658±124 versus 409±64, p=0.13, Students' t-test; FIGS. 2D and F, Table 2).

TABLE 2

Stereological counts (mean ± SEM) of newborn neurons (BrdU-NeuN-IR cells) in various layers of the dentate gyrus

|  | TBI-saline | TBI-Peptide 6 | p value |
|---|---|---|---|
| GCL | 1057(217) | 1901(265) | 0.03* |
| iGCL | 648(176) | 1225(169) | 0.03* |
| oGCL | 409(64) | 658(124) | 0.13 |
| EBI(0GCL/GCL) | 0.43(0.03) | 0.34(0.05) | 0.15 |

Where GCL: granule cell layer, iGCL: inner granule cell layer, oGCL: outer granule cell layer, EBI: ectopic birth index, p-value based on unpaired Student's t-test (*p < 0.05).

Together, this suggests that Peptide 6 caused a surge in the number of newborn mature neurons without increasing the number of progenitors. Whether this was due to better survival of new neurons or an increase in neuronal fate commitment of progenitors (or both) is unclear from these data.

Aberrant migration or "ectopic birth" of progenitors in the dentate gyrus:

A relatively small number of newborn cells (20-25%) are found in the oGCL (or migrating towards the molecular layer), while the rest remain in iGCL. A significant increase in number of progenitors in the oGCL is considered abnormal and has been implicated in abnormal connectivity such as that seen in Schizophrenia. Therefore, the number of BrdU-IR in the iGCL and oGCL were counted separately and calculated an "ectopic birth index" (EBI=oGCL/GCL) as described previously (FIG. 2 E-F). EBI analysis revealed that 40% of newborn cells in saline treated group were found in the oGCL compared with 32% in Peptide 6 treated animals (FIG. 2E and Table 1). Although this did not reach statistical significance (p=0.08, Student's t-test), it does suggest that an abnormally high proportion of new born cells are found in the oGCL in response to TBI, and that perhaps there is evidence, albeit weak, to suggest that Peptide 6 treatment corrects this aberrant migration or "ectopic birth". A similar, yet non-significant, trend was also seen in newborn mature neurons (43% in saline treated versus 34% in Peptide 6 treated, p=0.15, Student's t-test; FIG. 2F and Table 2).

TBI-Induced Reduction in Hippocampal Dendritic and Synaptic Density and its Recovery by Peptide 6:

The effect of TBI on dendritic network and synapses was further investigated in injured mice by measuring expression of MAP2 (a dendritic marker) and synaptophysin (a synaptic marker). Quantification of fluorescence intensity in DG (including molecular layer, granule cell layer, and hilus), CA3 and CA1 sub-regions revealed site and side-specific decreases in post-TBI mice (FIG. 3A). MAP2 expression was significantly decreased in all three hippocampal regions ipsilateral to the side of injury compared to the contralateral side (Bonferroni's post-hoc test, p<0.001 for DG, CA3, and CA1; FIG. 3B). Peptide 6 treatment increased MAP2 staining in the ipsilateral DG, CA3, and CA1 regions (an increase of 28.2%, 8.1%, and 21.1% respectively compared to ipsilateral saline treated TBI hippocampus). However, this difference was only statistically significant in DG region (Bonferroni's post-hoc test, p>0.05, Student's t-test, p=0.04; FIG. 3B, left panel) and a trend was evident in CA1 region (Bonferroni's post-hoc test, p>0.05, Student's t-test, p=0.06). Moreover, in Peptide 6 treated TBI mice, MAP2 intensity in DG did not differ significantly between ipsilateral and contralateral sides (FIG. 3B left panel). In the CA1 region, MAP2 expression was significantly higher on contralateral side in Peptide 6 treated mice than the saline treated group (FIG. 3B, right panel, Bonferroni's post-hoc test, p<0.001).

TBI-Induced Reduction in Hippocampal Synaptic Density and its Recovery by Peptide 6:

Synaptophysin expression was also significantly decreased in ipsilateral DG (Bonferroni's post-hoc test, p>0.05, Student's t-test, p=0.02) but not in CA3 and CA1 regions compared to the contralateral side in saline treated TBI mice (FIG. 4 A-B). Similar to MAP2 data, synaptophysin expression was also increased by 27.2%, 23.5%, and 40% in DG, CA3, and CA1 regions, respectively, on the ipsilateral side in Peptide 6 treated mice compared to controls; the differences were either statistically significant or a strong trend was evident (FIG. 4B; DG, Bonferroni's post-hoc test, p>0.05, Student's t-test, p=0.037; CA3, Bonferroni's post-hoc test, p>0.05, Student's t-test, p=0.09; CA1, Bonferroni's post-hoc test, p<0.05) Together, these findings suggest a "rescue effect" of Peptide 6 on TBI-induced decrease in the level of MAP2 and synaptophysin in various regions of the hippocampus.

Neuronal Loss in Ipsilateral Hippocampus and Parietal Cortex:

Neuronal loss in hippocampus and parietal cortex at 6 weeks post injury was determined (FIG. 5A). Quantitative cell counts of Nissl stained neurons revealed an 18% neuronal loss in the ipsilateral CA1 region of hippocampus in saline treated animals compared to contralateral side (83±5.7 versus 98±7.8, Bonferroni's post-hoc test, p<0.05, FIG. 5A, B). Interestingly, in Peptide 6 treated TBI-animals, this neuronal loss was significantly reduced in the ipsilateral CA1 region when compared with saline treated animals (100.5±8.3 versus 83±5.7, Bonferroni's post-hoc test, p<0.05, FIG. 5A-B)

There was a 37% loss of neurons in the ipsilateral parietal cortex, site of primary impact of TBI, compared to contralateral side in saline treated animals (94±1.2 versus 129±5.7, Bonferroni's post-hoc test, p<0.05, FIG. 5C, upper panel, ipsi; lower panel, contra; 5D). Similar to CA1 region, in Peptide 6 treated TBI-animals, neuronal loss was significantly stunted in the ipsilateral cortex when compared to saline treated mice (94±1.2 versus 126±12, Bonferroni's post-hoc test, p>0.05, Student's t-test, p=0.03, FIG. 5D).

Immediate-Early Gene Expression in Hippocampal Circuitry:

Changes in expression of immediate early genes (IEGs) such as FBJ osteosarcoma gene (c-fos), activity regulated cytoskeletal-associated protein (Arc) and early growth response 1 (Egr1 or Zif268) have been shown to be strongly coupled to neuronal activity associated with learning and memory and their expression in new born cells is detectable by 3-4 weeks. zif268-IR was measured in hippocampus of control and treated TBI-mice that were sacrificed within 3 hours of behavioral testing (FIG. 5E-F). Although DG and CA3 regions did not reveal any differences, an increase of over 129% was found in zif268-IR in CA1 region of TBI-mice treated with Peptide 6 when compared with controls, indicating increased activity in the traditional tri-synaptic pathway of hippocampal circuitry (FIG. 5F; Student's t-test, p<0.001).

Elevation of Alzheimer-Related Biomarkers in TBI-Mice:

Mild-to-moderate TBI is a risk factor for later development of AD. In order to assess if TBI-mice displayed molecular abnormalities of AD, the relative immunofluorescence of hyperphosphorylated tau and Aβ, two key hallmarks of AD, was measured. Quantitative immunofluorescence of PHF1 staining (against tau phosphorylated at serine 396 and 404) revealed significant elevation of hyperphosphorylated tau in ipsilateral CA1 region in both saline and Peptide 6 treated TBI mice (15% and 30% increase respectively, Bonferroni's post-hoc test, p<0.05, FIG. 7A,B). Similarly, staining with 4G8 (against Aβ and APP) revealed significant elevations in ipsilateral parietal cortex and CA1 regions (14% and 22% increase, respectively, Bonferroni's post-hoc test, p<0.05) compared to contralateral regions in saline treated TBI mice (FIG. 7B). There was no significant effect of Peptide 6 treatment on these AD-related biomarkers (Bonferroni's post-hoc test, p>0.05).

Behavioral Impairment in TBI-Mice and the Effect of Peptide 6 in Cognitive Recovery:

The effect of Peptide 6 on cognition was measured using a spatial reference memory test in the Morris water-maze (MWM). This spatial reference memory task assesses hippocampus-dependent reference memory in rodents, requiring that mice use a spatial navigational strategy to find a fixed submerged escape platform. For this purpose, mice were tested before injury and treatment (saline or Peptide 6) to establish baseline performances. The same mice were then injured and treated (saline or Peptide 6) and underwent another set of testing on the MWM (FIG. 6A). This allowed a study of the effect of Peptide 6 treatment on TBI mice. All groups learnt equally well under both testing conditions. Pre and post TBI testing revealed no differences in escape latencies during training phase of the MWM, i.e. in both instances, escape latencies decreased from day 1-day 4 of training (p>0.05, repeated measures ANOVA, FIG. 6C).

During probe trial, there was significant improvement in latency to target, percent time and percent distance travelled in the target quadrant in Peptide 6 treated animals when compared to saline treated TBI mice (p<0.01, one-way ANOVA, post hoc Tukey, FIG. 6D-F).

Cellular Response to Injury in the Hippocampus:

Moderate TBI induces rapid necrotic death of immature neurons in the hippocampus while mature granule neurons are largely spared. There is an enhanced level of cellular proliferation in key neurogenic areas of the brain following a variety of insults including stroke and trauma. A greater than 10-fold increase in BrdU-IR cells in the DG was reported in a lateral fluid percussion model of TBI. The rate of production of new cells in the DG is reported to peak between 3 to 7 days after injury and returns to basal level in 2 weeks, with new cells predominantly being microglia/macrophages and astrocytes at 72 hours of injury. There is evidence suggesting that even if new neurons are formed, they never survive to an age where they would be of functional consequence in the normal hippocampal circuitry.

A more recent study suggested no net increase in neurogenesis in a CCI mouse model of moderate TBI despite an increase in number of progenitors in the DG amounting to a "failed innate response". It is likely that these progenitors proliferate in an altered microenvironment which impairs their differentiation potential and/or integration in the local circuitry. In fact, levels of various neurotrophic factors correlate strongly with outcome in pediatric severe TBI.

Parallels Between TBI and AD

Mild to moderate TBI causes neurodegeneration of the type seen in AD and is considered a risk factor for AD in humans. In fact, there are many parallels between AD and TBI hippocampus at the cellular and molecular levels. For example, in both TBI and AD hippocampus, there is alteration in the levels of FGF2, NGF and BDNF. Moreover, like TBI, there is profound loss of dendritic and synaptic density in AD. The occurrence of neurofibrillary degeneration, however, is extremely difficult to demonstrate in rodents, which over the natural course of their lives, never develop classical AD pathology. This Alzheimer-type neurofibrillary degeneration is only seen in transgenic mice overexpressing mutated forms of human tau and or APP and at much older ages. The findings of elevated Aβ and hyperphosphorylated tau in ipsilateral CA1 regions of TBI mice in the current study are therefore, both interesting and remarkable.

Effect of TBI on Hippocampal Dendritic and Synaptic Density:

It is reported that within 3 hours of CCI induced injury in rodents, there is profound loss of MAP2 immunofluorescence in the apical dendrites of pyramidal neurons in the ipsilateral cortex that extends beyond the area of contusion. It is interesting to note that despite neuronal cell death in the hippocampus following TBI, the degree of cognitive impairment does not match with the amount of cell death. Even though, mature granule neurons are largely spared, there is dramatic drop in the density of dendritic spines and synapses in the surviving mature hippocampal neurons in moderate TBI after 72 hours of injury. The data in the present application confirms significant decreases in MAP2 staining throughout the hippocampus, including DG, CA1 and CA3 regions and similar decreases in synaptophysin levels in DG at 30 days following injury. This suggests that these changes persist in a chronic fashion and are likely to be involved in long-term cognitive deficits.

Behavioral Performance of TBI Mice:

The effect of Peptide 6 was evaluated on cognition using a spatial reference memory test in the MWM, the most frequently utilized protocol to study hippocampus dependent spatial learning and memory in rodents. The hippocampus processes information about the relationships among distal environmental cues into a spatial map where spatial coordinates of the submerged platform are encoded. The hippocampus is also crucial for memory storage, consolidation and restitution of the spatial information. This test was especially appropriate because TBI did not cause impairment in swim speeds in these mice. Pre injury training on the MWM showed no group differences in learning (FIG. 6C), establishing baseline uniformity in spatial encoding. This was maintained in the post TBI training phase with no differences between saline and Peptide 6 treated mice. However on probe trial, a significant improvement was found in measures of memory retention in Peptide 6 treated animals when compared with saline treatment.

CA1 Susceptibility in TBI:

Of the various hippocampal sub regions, CA1 is most vulnerable to hypoxic and ischemic insults when compared to DG and CA3. In the present invention, elevations of Alzheimer-type biomarkers were seen only in CA1 region. Although a significant decrease was found in synaptic and dendritic densities in all regions of the hippocampus, neuron cell loss was only significantly seen in CA1 region. This was not only prevented with Peptide 6 treatment, its effect on MAP2 and synaptophysin IR was most profound in the CA1 region. Consequently, there was also an upregulation of immediate-early gene expression in CA1 region of the hippocampus suggesting that mature CA1 neurons were actively participating in hippocampal dependent spatial paradigms. In MWM, activation of CA1 and CA3 regions is temporally and functionally distinct during different phases of the test. For example, when CA3 is experimentally blocked, direct activation of CA1 place cells might be sufficient for retrieval of spatial information during probe test. It is therefore, not surprising that in the present invention, TBI-mice did not display learning deficits but were impaired in recall.

What is claimed is:

1. A method of treating a subject having a tramatic brain injury, comprising the step of administering a therapeutic amount of a compound consisting of the sequence VGDGGLFEKKL (SEQ ID NO: 1).

2. The method of claim 1, wherein said compound is administered peripherally.

3. The method of claim 1, wherein said compound is administered subcutaneously.

4. The method of claim 1, wherein said compound is administered orally.

5. The method of claim 1, wherein said compound is administered intraperitoneally.

6. The method of claim 1, wherein the step of administering a therapeutic amount of a compound having the sequence VGDGGLFEKKL (SEQ ID NO: 1) is repeated daily.

7. The method of claim 6, wherein the step of administering a therapeutic amount of a compound consisting of the sequence VGDGGLFEKKL (SEQ ID NO: 1) is repeated daily over a period of thirty days.

* * * * *